(12) United States Patent
Nofzinger

(10) Patent No.: US 9,669,185 B2
(45) Date of Patent: *Jun. 6, 2017

(54) METHODS, DEVICES AND SYSTEMS FOR TREATING INSOMNIA BY INDUCING FRONTAL CEREBRAL HYPOTHERMIA

(71) Applicant: University of Pittsburgh—Of the Commonwealth System of Higher Education, Pittsburgh, PA (US)

(72) Inventor: Eric A. Nofzinger, Allison Park, PA (US)

(73) Assignee: University of Pittsburgh—Of the Commonwealth System of Higher Education, San Carlos, CA (US)

(*) Notice: Subject to any disclaimer, the term of this patent is extended or adjusted under 35 U.S.C. 154(b) by 36 days.

This patent is subject to a terminal disclaimer.

(21) Appl. No.: 14/749,590

(22) Filed: Jun. 24, 2015

(65) Prior Publication Data

US 2015/0290420 A1    Oct. 15, 2015

Related U.S. Application Data

(63) Continuation of application No. 13/868,015, filed on Apr. 22, 2013, now Pat. No. 9,089,400, which is a
(Continued)

(51) Int. Cl.
*A61F 7/00* (2006.01)
*A61M 21/02* (2006.01)
(Continued)

(52) U.S. Cl.
CPC ............ *A61M 21/02* (2013.01); *A61F 7/0085* (2013.01); *A61F 7/10* (2013.01); *A61M 19/00* (2013.01);
(Continued)

(58) Field of Classification Search
CPC .................... A61F 7/0085; A61F 7/001; A61F 2007/0007; A61F 2007/0008; A61M 21/00; A61M 2021/0066
See application file for complete search history.

(56) References Cited

U.S. PATENT DOCUMENTS

| 222,690 A | 12/1879 | Goldschmidt |
| 301,931 A | 7/1884 | Smith et al. |

(Continued)

FOREIGN PATENT DOCUMENTS

| EP | 1977710 | 10/2008 |
| EP | 2359781 | 8/2011 |

(Continued)

OTHER PUBLICATIONS

Adam et al.; Physiological and psychological differences between good and poor sleepers; J. psychiat. Res.; 20(4); pp. 301-316; 1986 (year of pub. sufficiently earlier than effective US filing date and any foreign priority date).

(Continued)

*Primary Examiner* — Kaitlyn Smith
(74) *Attorney, Agent, or Firm* — Shay Glenn LLP

(57) ABSTRACT

Method, systems and devices for treating insomnia by non-invasive hypothermic treatment are described. In general, these devices, systems and method enable cooling of the frontal cortex prior to and/or during sleep to enhance sleep, which may be particularly beneficial to treat insomnia.

34 Claims, 21 Drawing Sheets

Related U.S. Application Data continuation of application No. 13/019,477, filed on Feb. 2, 2011, now Pat. No. 8,425,583, and a continuation-in-part of application No. 11/788,694, filed on Apr. 20, 2007, now Pat. No. 8,236,038, said application No. 13/019,477 is a continuation-in-part of application No. 12/288,417, filed on Oct. 20, 2008, now Pat. No. 9,492,313.

(60) Provisional application No. 61/300,768, filed on Feb. 2, 2010, provisional application No. 60/793,680, filed on Apr. 20, 2006.

(51) Int. Cl.
 A61F 7/10 (2006.01)
 A61M 19/00 (2006.01)
 A61M 21/00 (2006.01)
 A61B 17/00 (2006.01)

(52) U.S. Cl.
 CPC ... A61M 21/00 (2013.01); A61B 2017/00132 (2013.01); A61F 7/007 (2013.01); A61F 2007/0002 (2013.01); A61F 2007/0007 (2013.01); A61F 2007/0056 (2013.01); A61F 2007/0075 (2013.01); A61F 2007/0095 (2013.01); A61M 2021/0066 (2013.01); A61M 2021/0083 (2013.01); A61M 2205/3606 (2013.01); A61M 2205/3626 (2013.01); A61M 2209/088 (2013.01); A61M 2210/06 (2013.01); A61M 2210/0693 (2013.01)

(56) References Cited

U.S. PATENT DOCUMENTS

| | | |
|---|---|---|
| 683,991 A | 10/1901 | Rowe |
| 737,473 A | 8/1903 | Porter |
| 805,371 A | 11/1905 | Meinecke et al. |
| 919,614 A | 4/1909 | Meinecke |
| 1,002,021 A | 8/1911 | Barnes |
| 1,127,221 A | 2/1915 | Finkelstein |
| 1,318,411 A | 10/1919 | Rozene |
| 1,322,984 A | 11/1919 | Wesley |
| 1,345,906 A | 7/1920 | Augustine |
| 1,511,775 A | 10/1924 | Frederic et al. |
| 1,522,295 A | 1/1925 | Gee |
| 1,567,931 A | 12/1925 | Epler |
| 1,743,244 A | 1/1930 | Shulman |
| 1,769,186 A | 7/1930 | Morris |
| 1,870,143 A | 8/1932 | Roux |
| 1,964,655 A | 6/1934 | Williamson |
| 2,049,723 A | 8/1936 | Pomeranz |
| 2,158,571 A | 5/1939 | Culp |
| 2,320,467 A | 6/1943 | Rabil |
| 2,726,658 A | 12/1955 | Chessey |
| 3,244,210 A | 4/1966 | Giacomo |
| 3,463,161 A | 8/1969 | Andrassy |
| 3,587,577 A | 6/1971 | Smirnov et al. |
| 3,696,814 A | 10/1972 | Umemoto |
| 3,717,145 A | 2/1973 | Berndt et al. |
| 3,895,638 A | 7/1975 | Ito |
| 3,908,655 A | 9/1975 | Lund |
| 3,979,345 A | 9/1976 | Yates et al. |
| 3,988,568 A | 10/1976 | Mantell |
| 4,118,946 A | 10/1978 | Tubin |
| 4,172,495 A | 10/1979 | Zebuhr et al. |
| 4,204,543 A | 5/1980 | Henderson |
| 4,356,709 A | 11/1982 | Alexander |
| 4,425,916 A | 1/1984 | Bowen |
| 4,483,021 A | 11/1984 | McCall |
| 4,566,455 A | 1/1986 | Kramer |
| 4,574,411 A | 3/1986 | Yagi |
| 4,691,762 A | 9/1987 | Elkins et al. |
| 4,742,827 A | 5/1988 | Lipton |
| 4,753,242 A | 6/1988 | Saggers |
| 4,765,338 A | 8/1988 | Turner et al. |
| 4,781,193 A | 11/1988 | Pagden |
| 4,854,319 A | 8/1989 | Tobin |
| 4,891,501 A | 1/1990 | Lipton |
| 4,920,963 A | 5/1990 | Brader |
| 4,961,422 A | 10/1990 | Marchosky et al. |
| 5,097,828 A | 3/1992 | Deutsch |
| 5,097,829 A | 3/1992 | Quisenberry |
| 5,163,425 A | 11/1992 | Nambu et al. |
| 5,183,058 A | 2/1993 | Janese |
| 5,197,466 A | 3/1993 | Marchosky et al. |
| 5,228,431 A | 7/1993 | Giarretto |
| 5,261,399 A | 11/1993 | Klatz et al. |
| 5,274,865 A | 1/1994 | Takehashi |
| 5,292,347 A | 3/1994 | Pompei |
| 5,305,470 A | 4/1994 | Mckay |
| 5,314,456 A | 5/1994 | Cohen |
| 5,327,585 A | 7/1994 | Karlan |
| 5,342,411 A | 8/1994 | Maxted et al. |
| 5,344,437 A | 9/1994 | Pistay |
| 5,356,426 A | 10/1994 | Delk et al. |
| 5,400,617 A | 3/1995 | Ragonesi et al. |
| 5,409,500 A | 4/1995 | Dyrek |
| 5,441,476 A | 8/1995 | Kitado et al. |
| 5,469,579 A | 11/1995 | Tremblay et al. |
| 5,531,777 A | 7/1996 | Goldstein et al. |
| 5,545,199 A | 8/1996 | Hudson |
| 5,603,728 A | 2/1997 | Pachys |
| 5,609,619 A | 3/1997 | Pompei |
| 5,643,336 A | 7/1997 | Lopez-Claros |
| 5,658,324 A | 8/1997 | Bailey, Sr. et al. |
| 5,715,533 A | 2/1998 | Stein |
| 5,755,756 A | 5/1998 | Freedman, Jr. et al. |
| 5,837,002 A | 11/1998 | Augustine et al. |
| 5,848,981 A | 12/1998 | Herbranson |
| 5,867,999 A | 2/1999 | Bratton et al. |
| 5,871,526 A | 2/1999 | Gibbs et al. |
| 5,895,418 A | 4/1999 | Saringer |
| 5,897,581 A | 4/1999 | Fronda et al. |
| 5,897,582 A | 4/1999 | Agnatovech et al. |
| 5,916,242 A | 6/1999 | Schwartz |
| 5,948,012 A | 9/1999 | Mahaffey et al. |
| 5,950,234 A | 9/1999 | Leong et al. |
| 5,957,963 A | 9/1999 | Dobak, III |
| 5,957,964 A | 9/1999 | Ceravolo |
| 6,010,528 A | 1/2000 | Augustine et al. |
| 6,017,337 A | 1/2000 | Pira |
| 6,030,412 A | 2/2000 | Klatz et al. |
| 6,051,019 A | 4/2000 | Dobak, III |
| 6,083,254 A | 7/2000 | Evans |
| 6,113,626 A | 9/2000 | Clifton et al. |
| 6,126,680 A | 10/2000 | Wass |
| 6,156,057 A | 12/2000 | Fox |
| 6,156,059 A | 12/2000 | Olofsson |
| 6,183,501 B1 | 2/2001 | Latham |
| 6,228,376 B1 | 5/2001 | Misumi et al. |
| 6,231,595 B1 | 5/2001 | Dobak, III |
| 6,248,126 B1 | 6/2001 | Lesser et al. |
| 6,277,143 B1 | 8/2001 | Klatz et al. |
| 6,295,819 B1 | 10/2001 | Mathiprakasam et al. |
| 6,312,453 B1 | 11/2001 | Stefanile et al. |
| 6,363,285 B1 | 3/2002 | Wey |
| 6,375,673 B1 | 4/2002 | Clifton et al. |
| 6,375,674 B1 | 4/2002 | Carson |
| 6,409,746 B1 | 6/2002 | Igaki et al. |
| 6,416,532 B1 | 7/2002 | Fallik |
| 6,461,379 B1 | 10/2002 | Carson et al. |
| 6,500,201 B1 | 12/2002 | Tsuchiya et al. |
| 6,511,502 B2 | 1/2003 | Fletcher |
| 6,516,624 B1 | 2/2003 | Ichigaya |
| 6,523,354 B1 | 2/2003 | Tolbert |
| 6,551,347 B1 | 4/2003 | Elkins |
| 6,554,787 B1 | 4/2003 | Griffin et al. |
| 6,581,400 B2 | 6/2003 | Augustine et al. |
| 6,599,312 B2 | 7/2003 | Dobak, III |
| 6,610,084 B1 | 8/2003 | Torres |
| 6,629,990 B2 | 10/2003 | Putz et al. |
| 6,669,715 B2 | 12/2003 | Hoglund et al. |

(56) References Cited

U.S. PATENT DOCUMENTS

| | | |
|---|---|---|
| 6,682,552 B2 | 1/2004 | Ramsden et al. |
| 6,692,518 B2 | 2/2004 | Carson |
| 6,699,267 B2 | 3/2004 | Voorhees et al. |
| 6,736,837 B2 | 5/2004 | Fox |
| 6,740,109 B2 | 5/2004 | Dobak, III |
| 6,740,110 B2 | 5/2004 | Babcock |
| 6,770,085 B1 | 8/2004 | Munson |
| 6,845,520 B2 | 1/2005 | Kim |
| 6,854,128 B1 | 2/2005 | Faulk |
| 6,881,219 B1 | 4/2005 | Agarwal et al. |
| 6,921,374 B2 | 7/2005 | Augustine |
| 6,929,656 B1 | 8/2005 | Lennox |
| 6,962,600 B2 | 11/2005 | Lennox et al. |
| 6,979,345 B2 | 12/2005 | Werneth |
| 7,008,445 B2 | 3/2006 | Lennox |
| 7,044,960 B2 | 5/2006 | Voorhees et al. |
| 7,052,509 B2 | 5/2006 | Lennox et al. |
| 7,056,334 B2 | 6/2006 | Lennox |
| 7,077,858 B2 | 7/2006 | Fletcher et al. |
| 7,087,075 B2 | 8/2006 | Briscoe et al. |
| 7,146,211 B2 | 12/2006 | Frei et al. |
| 7,152,412 B2 | 12/2006 | Harvie |
| 7,179,280 B2 | 2/2007 | Mills |
| 7,182,777 B2 | 2/2007 | Mills |
| 7,189,252 B2 | 3/2007 | Krueger |
| 7,229,468 B2 | 6/2007 | Wong, Jr. et al. |
| 7,309,348 B2 | 12/2007 | Streeter et al. |
| 7,559,907 B2 | 7/2009 | Krempel et al. |
| 7,637,931 B2 | 12/2009 | Heaton |
| 7,744,640 B1 | 6/2010 | Faries, Jr. et al. |
| 7,854,754 B2 | 12/2010 | Ting et al. |
| 7,875,066 B2 | 1/2011 | Cohen et al. |
| 7,877,827 B2 | 2/2011 | Marquette et al. |
| 7,909,861 B2 | 3/2011 | Balachandran et al. |
| 7,930,772 B2 | 4/2011 | Fontanez |
| 8,052,624 B2 | 11/2011 | Buchanan et al. |
| 8,236,038 B2 | 8/2012 | Nofzinger |
| 8,425,583 B2 | 4/2013 | Nofzinger |
| 8,784,293 B2 | 7/2014 | Berka et al. |
| 8,932,199 B2 * | 1/2015 | Berka .................. A61M 21/02 |
| | | 128/897 |
| 9,089,400 B2 | 7/2015 | Nofzinger |
| 2001/0000029 A1 | 3/2001 | Misumi et al. |
| 2001/0039442 A1 | 11/2001 | Gorge et al. |
| 2001/0045104 A1 | 11/2001 | Bailey, Sr. et al. |
| 2002/0026226 A1 | 2/2002 | Ein |
| 2002/0095198 A1 | 7/2002 | Whitebook et al. |
| 2002/0103520 A1 | 8/2002 | Latham |
| 2002/0156509 A1 | 10/2002 | Cheung |
| 2003/0109911 A1 | 6/2003 | Lachenbruch et al. |
| 2003/0130651 A1 | 7/2003 | Lennox |
| 2003/0149461 A1 | 8/2003 | Johnson |
| 2003/0171685 A1 | 9/2003 | Lesser et al. |
| 2003/0195439 A1 | 10/2003 | Caselnova |
| 2004/0010178 A1 | 1/2004 | Buckner |
| 2004/0024432 A1 | 2/2004 | Castilla |
| 2004/0049134 A1 | 3/2004 | Tosaya et al. |
| 2004/0059400 A1 | 3/2004 | Lin |
| 2004/0064170 A1 | 4/2004 | Radons et al. |
| 2004/0073280 A1 | 4/2004 | Dae et al. |
| 2004/0073281 A1 | 4/2004 | Caselnova |
| 2004/0159109 A1 | 8/2004 | Harvie |
| 2004/0171970 A1 | 9/2004 | Schleuniger et al. |
| 2004/0186541 A1 | 9/2004 | Agarwal et al. |
| 2004/0249427 A1 | 12/2004 | Nabilsi |
| 2005/0065584 A1 | 3/2005 | Schiff et al. |
| 2005/0087194 A1 | 4/2005 | Scott |
| 2005/0107851 A1 | 5/2005 | Taboada et al. |
| 2005/0131504 A1 | 6/2005 | Kim |
| 2005/0143797 A1 | 6/2005 | Parish et al. |
| 2006/0024358 A1 | 2/2006 | Santini et al. |
| 2006/0149119 A1 | 7/2006 | Wang |
| 2006/0161230 A1 | 7/2006 | Craven |
| 2006/0173396 A1 | 8/2006 | Hatamian et al. |
| 2006/0198874 A1 | 9/2006 | Stanley |
| 2006/0235495 A1 | 10/2006 | Tsai |
| 2006/0235498 A1 | 10/2006 | Mollendorf et al. |
| 2006/0293732 A1 | 12/2006 | Collins et al. |
| 2007/0010861 A1 | 1/2007 | Anderson et al. |
| 2007/0055330 A1 | 3/2007 | Rutherford |
| 2007/0123758 A1 | 5/2007 | Miesel et al. |
| 2007/0207220 A1 | 9/2007 | Luedtke et al. |
| 2007/0250138 A1 * | 10/2007 | Nofzinger ................ A61F 7/10 |
| | | 607/96 |
| 2007/0282249 A1 | 12/2007 | Quisenberry et al. |
| 2007/0282406 A1 | 12/2007 | Dow |
| 2008/0015665 A1 | 1/2008 | Lachenbruch |
| 2008/0033518 A1 | 2/2008 | Rousso et al. |
| 2008/0046026 A1 | 2/2008 | Pless et al. |
| 2008/0046047 A1 | 2/2008 | Jacobs |
| 2008/0097560 A1 | 4/2008 | Radziunas et al. |
| 2008/0097561 A1 | 4/2008 | Melsky et al. |
| 2008/0103568 A1 | 5/2008 | Dow |
| 2008/0140096 A1 | 6/2008 | Svadovskiy |
| 2008/0168605 A1 | 7/2008 | Wolske |
| 2008/0188915 A1 | 8/2008 | Mills et al. |
| 2008/0228248 A1 | 9/2008 | Guyuron et al. |
| 2008/0249520 A1 | 10/2008 | Dunning et al. |
| 2008/0269852 A1 | 10/2008 | Lennox et al. |
| 2008/0300529 A1 | 12/2008 | Reinstein |
| 2009/0049694 A1 | 2/2009 | Morris |
| 2009/0054958 A1 | 2/2009 | Nofzinger |
| 2009/0198311 A1 | 8/2009 | Johnson et al. |
| 2009/0236893 A1 | 9/2009 | Ehlers et al. |
| 2009/0306748 A1 | 12/2009 | Mollendorf et al. |
| 2009/0312676 A1 | 12/2009 | Rousso et al. |
| 2009/0312823 A1 | 12/2009 | Patience et al. |
| 2010/0030306 A1 | 2/2010 | Edelman et al. |
| 2010/0087701 A1 | 4/2010 | Berka et al. |
| 2010/0122398 A1 | 5/2010 | Luciano |
| 2010/0198281 A1 | 8/2010 | Chang et al. |
| 2010/0198318 A1 | 8/2010 | Rogers |
| 2010/0211142 A1 | 8/2010 | Rogers et al. |
| 2010/0312317 A1 | 12/2010 | Baltazar |
| 2010/0331752 A1 | 12/2010 | Cumming et al. |
| 2011/0125233 A1 | 5/2011 | Shen et al. |
| 2011/0282269 A1 | 11/2011 | Quisenberry et al. |
| 2012/0150268 A1 | 6/2012 | Doherty et al. |
| 2012/0302942 A1 | 11/2012 | DiPierro et al. |
| 2013/0103125 A1 | 4/2013 | Radspieler et al. |
| 2013/0131464 A1 | 5/2013 | Westbrook et al. |
| 2013/0289680 A1 | 10/2013 | Hasegawa |
| 2013/0303837 A1 * | 11/2013 | Berka .................. A61M 21/02 |
| | | 600/28 |
| 2014/0303428 A1 * | 10/2014 | Berka .................. A61M 21/02 |
| | | 600/27 |
| 2014/0343069 A1 | 11/2014 | Laiji et al. |
| 2015/0018905 A1 | 1/2015 | Nofzinger et al. |
| 2015/0238725 A1 | 8/2015 | Tucker et al. |
| 2016/0128864 A1 | 5/2016 | Nofzinger et al. |

FOREIGN PATENT DOCUMENTS

| | | |
|---|---|---|
| GB | 460200 A | 1/1937 |
| GB | 461294 A | 2/1937 |
| JP | 2-20522 | 2/1990 |
| JP | 10-192331 | 7/1998 |
| JP | 11-042282 | 2/1999 |
| JP | 2003164496 | 6/2003 |
| JP | 3730096 B | 10/2005 |
| JP | 2005274013 | 10/2005 |
| JP | 2006102020 | 4/2006 |
| WO | WO90/01911 A1 | 3/1990 |
| WO | WO92/20309 A1 | 11/1992 |
| WO | WO94/00086 A1 | 1/1994 |
| WO | WO95/10251 A1 | 4/1995 |
| WO | WO96/10379 A2 | 4/1996 |
| WO | WO96/31136 A1 | 10/1996 |
| WO | WO97/36560 A1 | 10/1997 |
| WO | WO98/56310 A1 | 12/1998 |
| WO | WO99/08632 A1 | 2/1999 |
| WO | WO00/03666 A1 | 1/2000 |
| WO | WO00/09052 A1 | 2/2000 |
| WO | WO01/39704 A1 | 6/2001 |

(56) References Cited

FOREIGN PATENT DOCUMENTS

| | | |
|---|---|---|
| WO | WO02/05736 A2 | 1/2002 |
| WO | WO02/34177 A1 | 5/2002 |
| WO | WO03/092539 A2 | 11/2003 |
| WO | WO2004/065862 A2 | 8/2004 |
| WO | WO2004/111741 A1 | 12/2004 |
| WO | WO2005/007060 A2 | 1/2005 |
| WO | WO2005/076806 A2 | 8/2005 |
| WO | WO2005/120428 A1 | 12/2005 |
| WO | WO2006/073915 A2 | 7/2006 |
| WO | WO2006/086086 A2 | 8/2006 |
| WO | WO2007/005026 A1 | 1/2007 |
| WO | WO2007/101039 A1 | 9/2007 |
| WO | WO2008/099017 A1 | 8/2008 |
| WO | WO2008/129357 A2 | 10/2008 |
| WO | WO2008/142650 A1 | 11/2008 |
| WO | WO2008/151260 A2 | 12/2008 |
| WO | WO2009/073208 A1 | 6/2009 |
| WO | WO2009/122336 A1 | 10/2009 |
| WO | WO2009/147413 A1 | 12/2009 |
| WO | WO2011/161571 A1 | 12/2011 |
| WO | WO2012/012683 A1 | 1/2012 |
| WO | WO2012/028730 A1 | 3/2012 |

OTHER PUBLICATIONS

Ahiska et al.; Control of a thermoelectric brain cooler by adaptive neuro-fuzzy interference system; Instrumentation Science and Technology; vol. 36(6); pp. 636-655; Oct. 2008.
Ahmed et al.; Development of a cooling unit for the emergency treatment of head injury; World Congress on Medical Physics and Biomedical Engineering 2006; IFMBE Proceedings; vol. 14(5); Track 19; pp. 3243-3246; Aug. 2006 (copyright 2007).
Alam et al.; Local preoptic / anterior hypothalamic warming alters spontaneous and evoked neuronal activity in the magno-cellular basal forebrain; Brian Research; 696; pp. 221-230; Oct. 1995.
Alam et al.; Preoptic / anterior hypothalamic neurons: thermosensitivity in rapid eye movement sleep; Am. J. Physiol. Regul. Integr. Comp. Physiol.; 269; pp. R1250-R1257; Nov. 1995.
Alfoldi et al.; Brian and core temperatures and peripheral vasomotion during sleep and wakefulness at various ambient temperatures in the rat; Pflugers Arch.; 417; pp. 336-341; Nov. 1990.
Aschoff, Circadian Rhythms in Man, Science, vol. 148, pp. 1427-1432, Jun. 11, 1965.
Baker et al.; Persistence of sleep-temperature coupling after suprachiasmatic nuclei lesions in rats; Am. J. Physiol. Regul. Integr. Comp. Physiol.; 289(3); pp. R827-R838; Sep. 2005.
Boulant et al.; Hypothalamic neuronal responses to peripheral and deep-body temperatures; Am. J. of Physiol.; 225(6); pp. 1371-1374; Dec. 1973.
Boulant et al.; Temperature receptors in the central nervous system; Ann. Rev. Physiol.; 48; pp. 639-654; 1986 (year of pub. sufficiently earlier than effective US filing date and any foreign priority date).
Boulant et al.; The effects of spinal and skin temperatures on the firing rate and thermosensitivity of preoptic neurones; J. Physiol.; 240(3); pp. 639-660; Aug. 1974.
Boulant; Hypothalamic mechanisms in thermoregulation; Fed. Proc.; 40(14); pp. 2843-2850; Dec. 1981.
Brown; Toe temperature change: a measure of sleep onset?; Walking and Sleeping; 3(4); pp. 353-359; Sep.-Dec. 1979.
Clarkson et al.; Thermal neutral temperature of rats in helium-oxygen, argon-oxygen, and air; Am. J. Physiol.; 222(6); pp. 1494-1498; Jun. 1972.
Crawshaw et al.; Effect of local cooling on sweating rate and cold sensation; Pfugers Arch.; 354(1); pp. 19-27; 1975 (year of pub. sufficiently earlier than effective US filing date and any foreign priority date).
Diao et al., Cooling and Rewarming for Brain Ischemia or Injury: Theoretical Analysis, Annals of Biomedical Engineering, vol. 31, p. 346-353, Mar. 2003.

Gong et al.; Sleep-related c-Fos protien expression in the preoptic hypothalamus: effects of ambient warming; Am. J. Physiol. Regul. Integr. Comp. Physiol.; 279(6); pp. R2079-R2088; Dec. 2000.
Gordon; Relationship between preferred ambient temperature and autonomic thermoregulatory function in rat; Am. J. Physiol. Regul. Integr. Comp. Physiol.; 252; pp. R1130-R1137; 1987 (year of pub. sufficiently earlier than effective US filing date and any foreign priority date).
Gulia et al.; Ambient temperature related sleep changes in rats neonatally treated with capsaicin; Physiol. Behav.; 85(4); pp. 414-418; Jul. 21, 2005.
Guzman-Marin et al.; Discharge modulation of rat dorsal raphe neurons during sleep and waking: effects of preoptic / basal forebrain warming; Brain Res.; 875(1-2); pp. 23-34; Sep. 1, 2000.
Van Someren; More than a maker: interaction between the ciradian regulation of temperature and sleep, age-related changes, and treatment possibilities; Chronobiol. Int.; 17(3).
Haskell et al.; The effects of high and low ambient temperatures on human sleep stages; Electroencephalogr. Clin. Neurophysiol.; 51(5); pp. 494-501; May 1981.
Hayashi et al., The alerting effects of caffeine, bright light and face washing after a short daytime nap, Clinical Neurophysiology, 114(12), pp. 2268-2278, Dec. 2003.
Hensley et al.; 50 years of computer simulation of the human thermoregulatory system; J. Biomech. Eng.; 135(2); pp. 021005-1-021005-9; Feb. 2013.
Herrington; The heat regulation of small laboratory animals at various environmental temperatures; Am. J. of Physiol.; 129; pp. 123-139; Mar. 31, 1940.
Heuvel et al.; Changes in sleepiness and body temperature precede nocturnal sleep onset: evidence from a polsomnographic study in young men; J. Sleep Res.; 7(3); pp. 159-166; Sep. 1998.
Horne et al., Vehicle accidents related to sleep: a review, Occup Environ Med, vol. 56(5), pp. 289-294 (full text version 13 pgs.), May 1999.
Horne et al.; Exercise and sleep: body-heating effects; Sleep; 6(1); pp. 36-46; 1983 (year of pub. sufficiently earlier than effective US filing date and any foreign priority date).
Horne et al.; Slow wave sleep elevations after body heating: proximity to sleep and effects of aspirin; Sleep; 10(4); pp. 383-392; Aug. 1987.
Iber et al.; The AASM manual for the scoring of sleep and associatted events. The rules, terminology and technical specifications; Westchester, IL; © 2007; 57 pages; Oct. 28, 2014; retrieved from the internet (http://www.nswo.nl/userfiles/files/AASM%20-%20Manual%20for%20the%20Scoring%20ofSleep%20and%20Associted%20Events%20-%2005-2007_2.pdf).
Iwata et al., Brain temperature in newborn piglets under selective head cooling with minimal systemic hypothermia, Pediatrics International, 45(2), pp. 163-168; Apr. 2003.
John et al.; Changes in sleep-wakefulness after kainic acid lesion of the preoptic area in rats; Jpn J. Physiol.; 44; pp. 231-242; 1994 (year of pub. sufficiently earlier than effective US filing date and any foreign priority date).
John et al.; Effect of NMDA lesion of the medial preoptic neurons on sleep and other functions; Sleep; 21(6); pp. 587-598; Sep. 15, 1998.
Khubchandani et al.; Functional MRI shows activation of the medial preoptic area during sleep; NeuroImage; 26; pp. 29-35; May 15, 2005.
Krauchi et al., Circadian rhythm of heat production, heart rate, and skin and core temperature under unmasking conditions in men, American Physiological Society, 267 (3 Pt 2), pp. R819-R829, Sep. 1994.
Krauchi et al., Circadian Clues to Sleep Onset Mechanisms, Neuropsychopharmacology, vol. 25, No. S5, pp. S92-S96, Nov. 2001.
Krauchi et al., Functional link between distal vasodilation and sleep-onset latency, Am. J. Physiol. Regulatory Integrative Comp. Physiol., 278(3), pp. R741-R748, Mar. 2000.
Krauchi et al., Warm feet promote the rapid onset of sleep, Nature, vol. 401, pp. 36-37, Sep. 2, 1999.

(56) References Cited

OTHER PUBLICATIONS

Krilowicz et al.; Regulation of posterior lateral hypothalamic arousal related neuronal discharge by preoptic anterior hypothalamic warming; Brain Res.; 668(1-2); pp. 30-38; Dec. 30, 1994.
Kumar et al.; Ambient temperature that induces maximum sleep in rats; Physiol. Behav.; 98(1-2); pp. 186-191; Aug. 4, 2009.
Szymusiak et al.; Maximal REM sleep time defines a narrower thermoneutral zone than does minimal metabolic rate; Physiol. Behav.; 26(4); pp. 687-690; Apr. 1981.
Szymusiak et al.; Sleep suppression following kainic acid-induced lesions of the basal forebrain; Exp. Neurol.; 94(3); pp. 598-614; Dec. 1986.
Kumar; Body temperature and sleep: are they controlled by the same mechanism?; Sleep and Biological Rhythms; 2(2); pp. 103-124; Jun. 2004.
Lack et al.; The rhythms of human sleep propensity and core body temperature; J. Sleep Res.; 5(1); pp. 1-11; Mar. 1996.
Lee et al.; Thermal spot over human body surface (part 1) regional difference in cold spot distribution; J. Human and Living Environment; 2(1); pp. 30-36; 1995 (year of pub. sufficiently earlier than effective US filing date and any foreign priority date).
Leshner et al., Manifestations and Management of Chronic Insomnia in Adults, NIH State-of-the-Science Conference, Final Panel Statement, Bethesda, MD, 36 pgs., Jun. 13-15, 2005.
Libert et al.; Effect of continuous heat exposure on sleep stages in humans; Sleep; 11(2); pp. 195-209; Apr. 1988.
Wang et al., Rapid and selective cerebral hypothermia achieved using a cooling helmet, Journal of Neurosurgery, vol. 100 No. 2, pp. 272-277 (full text version 18 pgs), Feb. 2004.
Von Economo; Sleep as a problem of localization; The Journal of Nervous and Mental Disease; 71(3); pp. 1-5; Mar. 1930.
McGinity et al.; Hypothalamic regulation of sleep and arousal; Frontiers in Bioscience; 8; pp. s1074-s1083; Sep. 1, 2003.
McGinity et al.; Keeping cool: a hypothesis about the mechanisms and functions of slow-wave sleep; TINS; 13(12); pp. 480-487; Dec. 1990.
McGinity et al.; Sleep suppression after basal forebrain lesions in the cat; Science; 160(3833); pp. 1253-1255; Jun. 14, 1968.
McKenzie/Mini-Mitter Co.; Mini-Logger® Series 2000, Physiological Data Logging Device; 510K Summary and Premarket Notification (No. K033534); 10 pgs.; Apr. 22, 2004.
Methipara et al.; Preoptic area warming inhibits wake-active neurons in the perifornical lateral hypothalamus; Brain Res.; 960(1-2); pp. 165-173; Jan. 17, 2003.
Morairty et al.; Selective increases in non-rapid eye movement sleep following whole body heating in rats; Brain Res.; 617(1); pp. 10-16; Jul. 16, 1993.
Nadel et al.; Differential thermal sensitivity in the human skin; Pflugers Arch.; 340(1); pp. 71-76; 1973 (year of pub. sufficiently earlier than effective US filing date and any foreign priority date).
Szymusiak et al.; Sleep-related neuronal discharge in the basal forebrain of cats; Brain Res.; 370(1); pp. 82-92; Apr. 2, 1986.
Nakayama et al.; Thermal stimulation of electrical activity of single units of the preoptic region; Am. J. Physiol.; 204(6); pp. 1122-1126; 1963 (year of pub. sufficiently earlier than effective US filing date and any foreign priority date).
Nakayama; Single unit activity of anterior hypothalamus during local heating; Science; 134(3478); pp. 560-561; Aug. 25, 1961.
Nauta; Hypothalamic regulation of sleep in rats. An experimental study; J. Neurophysiol.; 9; pp. 285-316; Jul. 1946.
Nofzinger et al., Functional Neuroimaging Evidence for Hyperarousal in Insomnia, Am J Psychiatry, 161(11), pp. 2126-2128, Nov. 2004.
Nofzinger et al.; Alterations in regional cerebral glucose metabolism across waking and non-rapid eye movement sleep in depression; Arch. Gen. Psychiatry; 62(4); pp. 387-396; Apr. 2005.
Nofzinger et al.; Frontal cerebral hypothermia: A new approach to the treatment of insomnia; Sleep; Abstract Suppl.; vol. 32; abstract No. 0881; pp. A287-A288; Jun. 2009.
Nofzinger et al.; Regional cerebral metabolic correlates of WASO during NREM sleep in insomnia; J. Clinical Sleep Med.; 2(3); pp. 316-322; Jul. 2006.
Nofzinger/Cereve; SBIR/STTR Grant Submission; Feasibility of frontal cerebral hypothermia as a treatment for insomnia; submitted Dec. 9, 2008.
Obal et al.; Changes in the brain and core temperatures in relation to the various arousal states in rats in the light and dark periods of the day; Pflugers Arch.; 404(1); pp. 73-79; May 1985.
Olympic Medical; Olympic Cool-Cap System (Product Brochure); 4 pgs.; (year of pub. sufficiently earlier than effective US filing date and any foreign priority date) 2007.
Osborne et al.; Effects of hypothalamic lesions on the body temperature rhythm of the golden hamster; Neuroreport; 6(16); pp. 2187-2192; Nov. 13, 1995.
Parmeggiani et al; Hypothalamic temperature during the sleep cycle at different ambient temperatures; Electroencephalogr. and Clin. Neurophysiol.; 38(6); pp. 589-596; Jun. 1975.
Parmeggiani; Interaction between sleep and thermoregulation: an aspect of the control of behavioral states; Sleep; 10(5); pp. 426-435; Oct. 1987.
Parmeggiani et al.; Sleep and environmental temperature; Arch. Ital. Biol.; 108(2); pp. 369-387; Apr. 1970.
Poole et al.; Body temperature regulation and thermoneutrality in rats; Q. J. Exp. Physiol. Cogn. Med. Sci.; 62(2); pp. 143-149; Apr. 1977.
Ray et al.; Changes in sleep-wakefulness in the medial preoptic area lesioned rats: role of thermal preference; Behav. Brain Res.; 158(1); pp. 43-52; Mar. 7, 2005.
Ray et al.; Changes in thermal preference, sleep-wakefulness, body temperature and locomotor activity of rats during continuous recording for 24 hours; Behav. Brain Res.; 154(2); pp. 519-526; Oct. 5, 2004.
Raymann et al.; Diminished capability to recognize the optimal temperature for sleep initiation may contribute to poor sleep in elderly people; Sleep; 31(9); pp. 1301-1309; Sep. 2008.
Raymann et al.; Skin deep: enhanced sleep depth by cutaneous temperature manipulation; Brain; 131(PT 2); pp. 500-513; Feb. 2008.
Reyner et al., Evaluation of 'In-Car' Countermeasures to Sleepiness: Cold Air and Radio, Sleep, vol. 21 (1), pp. 46-50, (year of pub. sufficiently earlier than effective US filing date and any foreign priority date) 1998.
Romanovsky et al.; Molecular biology of thermoregulation selected contribution: ambient temperature for experiments in rats: a new method for determining the zone of thermal neutrality; J. Appl. Phsyiol.; 92(6); pp. 2667-2679; Jun. 2002.
Schmidek et al.; Influence of environmental temperature on the sleep-wakefulness cycle in the rat; Physiol. Behav.; 8(2); pp. 363-371; Feb. 1972.
Setokawa et al.; Facilitating effect of cooling the occipital region on nocturnal sleep; Sleep and Biological Rhythms; 5(3); pp. 166-172; Jul. 2007.
Sewitch; Slow wave sleep deficiency insomnia: a problem in thermo-downregulation at sleep onset; Phychophsyiology; 24(2); pp. 200-215; Mar. 1987.
Shapiro et al.; Thermal load alters sleep; Biol. Psychiatry; 26(7); pp. 736-740; Nov. 1989.
Sherin et al.; Activation of ventrolateral preoptic neurons during sleep; Science; 271(5246); pp. 216-219; Jan. 12, 1996.
Srividya et al.; Differences in the effects of medial and lateral preoptic lesions on thermoregulation and sleep in rats; Neuroscience; 139(3); pp. 853-864; 2006 (year of pub. sufficiently earlier than effective US filing date and any foreign priority date).
Srividya et al.; Sleep changes produced by destruction of medial septal neurons in rats; Neorreport; 15(11); pp. 1831-1835; Aug. 2004.
Sterman e tal.; Forebrain inhibitory mechanisms: sleep patterns induced by basal forebrain stimulation in the behaving cat; Exp. Neurol.; 6; pp. 103-117; Aug. 1962.
Stevens et al.; Regional sensitivity and spatial summation in the warmth sense; Physiol. Behav.; 13(6); pp. 825-836; Dec. 1974.

(56) References Cited

OTHER PUBLICATIONS

Stevens et al.; Temperature sensitivity of the body surface over the life span; Somatosens. Mot. Res.; 15(1); pp. 13-28; 1998 (year of pub. sufficiently earlier than effective US filing date and any foreign priority date).

Szymusiak et al.; Ambient temperature-dependence of sleep disturbances produced by basal forebrain damage in rats; Brain Res. Bull.; 12(3); pp. 295-305; Mar. 1984.

Walker et al.; U.S. Appl. No. 14/758,438 entitled "Systems for enhancing sleep," filed Jun. 29, 2015.

Hajos et al.; The capsaicin sensitivity of the preoptic region is preserved in adult rats pretreated as neonates, but lost in rats pretreated as adults; Naunyn-Schmiedeberg's Arch. Pharmacol.; 324(3); pp. 219-222; Nov. 1983.

Lu et al.; Effect of lesions of the ventrolateral preoptic nucleus on NREM and REM sleep; J. Neurosci.; 20(10); pp. 3830-3842; May 15, 2000.

Mahapatra et al.; Changes in sleep on chronic exposure to warm and cold ambient temperatures; Physiol. Behav.; 84(2); pp. 287-294; Feb. 15, 2005.

Tamura et al.; Thermal spot over human body surface (part II) regional diference in warm spot distribution; J. Human and Living Environment; 2(1); pp. 37-42; 1995 (year of pub. sufficiently earlier than effective US filing date and any foreign priority date).

Van Someren; Mechanisms and functions of coupling between sleep and temperature rhythms; Progress in Brain research; 153; pp. 309-324; 2006 (year of pub. sufficiently earlier than effective US filing date and any foreign priority date).

Thannickal et al.; Effect of ambient temperature on brain temperature and sleep-wakefulness in medial preoptic area lesioned rats; Indian J. Pharmacol.; 46(3); pp. 287-297; Jul. 2002.

\* cited by examiner

Reductions in waking after
sleep onset (minutes)

Increases in delta
power during sleep

Reductions in relative regional metabolism

METHODS, DEVICES AND SYSTEMS FOR TREATING INSOMNIA BY INDUCING FRONTAL CEREBRAL HYPOTHERMIA

CROSS REFERENCE TO RELATED APPLICATIONS

This patent application is a continuation of U.S. patent application Ser. No. 13/868,015, filed Apr. 22, 2013, titled "METHODS, DEVICES AND SYSTEMS FOR TREATING INSOMNIA BY INDUCING FRONTAL CEREBRAL HYPOTHERMIA," now U.S. Pat. No. 9,089,400 which is a continuation of U.S. patent application Ser. No. 13/019,477, filed Feb. 2, 2011, titled "METHODS, DEVICES AND SYSTEMS FOR TREATING INSOMNIA BY INDUCING FRONTAL CEREBRAL HYPOTHERMIA," now U.S. Pat. No. 8,425,583, which claims priority to U.S. Provisional Patent Application No. 61/300,768, filed Feb. 2, 2010, each of which is herein incorporated by reference in its entirety.

U.S. patent application Ser. No. 13/019,477 also claims priority as a continuation-in-part of U.S. patent application Ser. No. 11/788,694, filed Apr. 20, 2007, titled "METHOD AND APPARATUS OF NONINVASIVE, REGIONAL BRAIN THERMAL STIMULATION FOR THE TREATMENT OF NEUROLOGICAL DISORDERS," now U.S. Pat. No. 8,236,038, which claims priority to U.S. Provisional Patent Application No. 60/793,680, filed on Apr. 20, 2006, each of which is herein incorporated by reference in its entirety.

U.S. patent application Ser. No. 13/019,477 also claims priority as a continuation-in-part of U.S. patent application Ser. No. 12/288,417, filed Oct. 20, 2008, titled "METHOD AND APPARATUS OF NONINVASIVE, REGIONAL BRAIN THERMAL STIMULATION FOR THE TREATMENT OF NEUROLOGICAL DISORDERS," now U.S. Pat. No. 9,492,213, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are methods, devices and systems for the treatment of insomnia. In particular, described herein are methods, devices and systems for treatment of insomnia by cooling the frontal (e.g. prefrontal) cortex.

BACKGROUND

Insomnia is most often described as the inability to fall asleep easily, to stay asleep or to have quality sleep in an individual with adequate sleep opportunity. In the U.S., population-based estimates of either chronic or transient insomnia range from 10 to 40% of the population, or 30 to 120 million adults in the United States. Similar prevalence estimates have been reported in Europe and Asia. Across studies, there are two age peaks: 45-64 years of age and 85 years and older. Women are 1.3 to 2 times more likely to report trouble sleeping than men, as are those who are divorced or widowed, and have less education. In the U.S., the economic burden of insomnia approaches $100 billion, in direct health care costs, functional impairment, increased risk of mental health problems, lost productivity, worker absenteeism and excess health care utilization. It is recognized as a public health problem, contributing to more than twice the number of medical errors attributed to health care workers without insomnia episodes. Currently available treatments for insomnia, however, are not entirely satisfactory for a variety of reasons. Sedative-hypnotics are not a complete solution to the problem of insomnia as they are associated with significant adverse events such as the potential for addiction/dependence, memory loss, confusional arousals, sleep walking and problems with coordination that can lead to falls and hip fractures. The majority of insomnia patients would prefer a non-pharmaceutical approach to their insomnia complaints. Cognitive behavior therapy, while effective, is an expensive and labor intensive treatment that is not widely available and is not always covered by health insurance. Over-the-counter approaches to the treatment of insomnia including a variety of medications and devices suffer from inadequate clinical studies demonstrating significant effects in insomnia patients, as well as potentially dangerous side effects. A large need exists, therefore, for a safe, effective, non-invasive, non-pharmaceutical device for the treatment of insomnia.

Recent advances have been made in the neurobiology of sleep and in the neurobiology of insomnia that can inform innovative treatments for insomnia. Considerable evidence suggests that sleep may serve a restorative function. An EEG marker of sleep homeostasis is EEG spectral power in the delta frequency range (1-4 Hz). The homeostatic sleep drive may involve the restoration of brain energy metabolism through the replenishment of brain glycogen stores that are depleted during wakefulness. This function may have some regional specificity. A frontal dominance of EEG spectral power in the delta EEG spectral power range has been reported. A frontal predominance for the increase in delta power following sleep loss has also been reported. This region of cortex plays a prominent role in waking executive functions which are preferentially impaired following sleep deprivation. Evidence such as this, suggests that sleep is essential for optimal executive behavior and that the mechanism involves the frontal cortex.

"Hyperarousal", on a variety of physiological levels, represents the current leading pathophysiological model of insomnia. Insomnia patients have been shown to have increased whole brain metabolism across waking and sleep in relation to healthy subjects; resting metabolic rate, heart rate and sympathovagal tone in HRV, cortisol secretion in the evening and early sleep hours, beta EEG activity during NREM sleep, increased levels of cortical glucose metabolism, especially in the frontal cortex, associated with higher levels of wakefulness after sleep onset, impairments in the normal drop in core body temperature around the sleep onset period; and cognitive hyperarousal resting on the pre-sleep thoughts of insomnia patients, often described as "racing," unstoppable, and sleep-focused. Recent evidence also suggests that insomnia sufferers demonstrate selective attention directed toward sleep and bed-related stimuli, which may lead to a self-reinforcing feedback loop of conditioned arousal, poor sleep, and impaired waking function. Insomnia patients have demonstrated increases in beta EEG spectral power that correlate with increased metabolism in the ventromedial prefrontal cortex during NREM sleep. Improvements in sleep in insomnia patients have been associated with improvements in prefrontal cortex function as measured by functional neuroimaging.

A decline in metabolism in the prefrontal cortex, therefore, appears to be important for the normal function of sleep and hypermetabolism in this region may interfere with this normal function of sleep in insomnia patients. Interventions designed to reduce elevated metabolism in the prefrontal cortex may improve sleep in insomnia patients.

Several lines of evidence suggest that application of a cooling stimulus to the scalp may reduce metabolism in the cortex underlying the stimulus. Studies have shown that the application of a cooling stimulus to the scalp decreases brain temperature in the underlying cortex in both animals and humans. In a study in pigs, even a mild surface cooling of 15 degrees C. was associated with cooling of the scalp and superficial brain to 35 degrees C. In this study, there was a notable differential effect of surface cooling on superficial vs. deep brain tissue, with superficial brain tissue cooled to a greater degree than deep brain tissue. In a human study, Wang et al were able to decrease surface brain temperatures by an average of 1.84 degrees C. within 1 hour of subjects wearing a whole head cooling helmet. Biomedical engineering models demonstrate that cooling of the brain gray matter can be achieved by selective head cooling on the surface. These lines of evidence support the concept that application of a cooling stimulus at the scalp will be associated with reductions in metabolism in the underlying cortex.

Cerebral hypothermia is an intervention that has previously been used to treat other medical disorders due to its neuroprotective effects. Therapeutic hypothermia after global and focal ischemic and other neurotoxic events such as head trauma, stroke and neuronal insult during cardiopulmonary surgery has shown beneficial results in controlled animal and human studies. Preclinical studies have shown many neuroprotective effects of brain cooling. These include: metabolism, pH, neurotransmitter levels, free fatty acids, blood-brain barrier, edema, glucose metabolism, cerebral blood flow, free radical activation, lipid peroxidation, calcium accumulation, protein synthesis, protein kinase-C activity, leukocyte accumulation, platelet function, NMDA neurotoxicity, growth factors, cytoskeletal proteins, calcium-dependent protein phosphorylation, heat shock protein, immediate early genes, NOS activity, and MMP expression. It is conceivable that the neuroprotective benefits of cerebral hypothermia may aid patients with sleep disorders, including insomnia. Pathophysiologic models of the adverse events associated with sleep disorders are beginning to focus on the potential neuronal toxicity of having a sleep disorder. That this may occur in insomnia is suggested by findings of hypercortisolemia in insomnia patients in the evening and early hours of sleep and known adverse effects of hypercortisolemia on neuronal function. One preliminary study has demonstrated reduced volumes of the hippocampus in insomnia patients. This may be the result of neurotoxic factors.

Reducing hypermetabolism in the frontal cortex of insomnia patients during both the pre-sleep period and during sleep may reduce cognitive hyperarousal reported by insomnia patients. Cerebral localization of this is hypothesized to occur in the prefrontal cortex given its role in executive function and ruminative cognitions.

Application of a cooling stimulus to the frontal scalp area may also facilitate the normative changes in thermoregulation associated with sleep onset. Heat loss, via selective vasodilatation of distal skin regions (measured by the distal minus proximal skin temperature gradient (DPG), seems to be a crucial process for the circadian regulation of core body temperature (CBT) and sleepiness. Increased DPG before lights off has been noted to promote a rapid onset of sleep, suggesting a link between thermoregulatory and arousal (sleepiness) systems. As noted above, impairments in the normal drop in core body temperature around the sleep onset period has been demonstrated in insomnia patients. A device that produces heat loss, especially through the periphery, therefore, may improve sleep in insomnia patients.

Recent studies show that difficulty sleeping can be associated with increased brain metabolic activity especially in the frontal cortex. Patent application Ser. No. 11/788,694, filed Apr. 20, 2007, titled "Method and Apparatus of Noninvasive, Regional Brain Thermal Stimuli for the Treatment of Neurological Disorders," now U.S. Pat. No. 8,236,038, which was previously incorporated by reference, described a method and apparatus of noninvasive, regional brain thermal stimuli for the treatment of neurological disorders. Functional neuroimaging studies have shown that a noninvasive device applying a hypothermic stimulus to the scalp overlying the frontal cortex of the brain ("frontal hypothermia") reduced cerebral metabolic activity in insomnia patients during sleep, especially in the frontal cortex underlying the hypothermic pad. While these studies suggest that frontal hypothermia may be helpful in the clinical management of insomnia patients, the most appropriate parameters for the application of the device have not yet been fully worked out.

Preliminary data using frontal hypothermia suggests that it reduces relative metabolism in a region of cerebral cortex underlying the scalp where the device is applied. Application of the device would not necessarily be limited to the condition of insomnia, but could be applied to diverse neuropsychiatric disorders, each of which may have insomnia as a contributing component or which may be characterized by its own abnormal pattern of cerebral metabolism.

Several disorders have been shown to have insomnia as a co-morbid condition and/or relatively specific alterations in cerebral metabolism that may benefit from treatment with a frontal hypothermia device. These co-morbid conditions make medication treatment even more difficult, because these patients are often already on multiple other medications, some of which have sleep effects themselves. Co-morbid insomnia itself has been little studied with any form of treatment. Depression is associated with severe sleep disturbances including difficulty falling asleep, difficulty staying asleep, early morning awakening, or nonrestorative sleep. Functional neuroimaging studies have shown alterations in the normal reduction in prefrontal cortex metabolism from waking to NREM sleep. The lifetime prevalence of depression in the United States is 17.1% or currently 52 million individuals suggesting that this is a significant problem. The neurobiology of sleep problems in patients with chronic pain share significant overlaps with those of insomnia suggesting another medical disorder that may benefit from the frontal hypothermia device. The most common causes of pain that disrupt sleep include back pain (cost to society estimated to exceed $100 billion each year), headaches (50% of whom sleep disturbances trigger headaches and 71% of migraine sufferers have migraines that awaken them from sleep), fibromyalgia, and arthritis (osteoarthritis, rheumatoid arthritis and autoimmune diseases such as lupus). Chronic pain prevalence estimates in the United States are 10.1% for back pain, 7.1% for pain in the legs/feet, 4.1% for pain in the arms/hands, and 3.5% for headache. Chronic regional and widespread pain, are reported by 11.0% and 3.6% of respondents, respectively. Based on US Census data, this would translate into an additional market of over 50 million individuals. 70-91% of patients with post-traumatic stress disorder (PTSD) have difficulty falling or staying asleep. Medical treatments for the sleep problems in PTSD have revolved around medication management, which have associated adverse events. Studies conducted as part of the National Comorbidity Survey (NCS) have reported the prevalence of lifetime PTSD in the United States as 7.8 percent or currently a market of over 23 million individuals.

Aside from a primary, stand alone therapy for insomnia, this device may also benefit insomnia patients who are partial responders to traditional sedative-hypnotic therapy for insomnia or from cognitive-behavior therapy for insomnia. While clinical trial data suggest that approved hypnotics show statistically significant improvements in about ⅔rds of patients, significantly fewer patients report full remission of symptoms. This suggests that about ⅔rds of patients who are prescribed hypnotics would be non-responders or partial responders to these treatments and as such may benefit from adjunctive therapy with frontal hypothermia insomnia device, such as the devices and systems described herein.

Thus, there is a substantial need to provide methods, devices and systems for effectively creating frontal hypothermia to treat insomnia. The methods, devices and systems described herein may address many of the needs and issues described above.

SUMMARY OF THE DISCLOSURE

In general, described herein are methods, devices and systems for applying hypothermal therapy within highly controlled parameters to the skin over the prefrontal cortex in order to cool the prefrontal cortex and thereby reduce metabolism of this brain region. As described in greater detail below, hypothermic therapy of the prefrontal cortex may ameliorate insomnia. Thus, in many of the therapeutic methods described herein, a device or system includes an applicator having a thermal transfer region (e.g., pad, etc.) that is configured to contact, or be placed in thermal contact, with the patient's skin; specifically the skin over the prefrontal cortex. The applicator may be a mask or garment, and the thermal transfer region may be cooled and temperature controlled by any appropriate means, including fluid cooled (e.g., water cooled) or solid-state (e.g., Peltier device) or some combination thereof.

For example, described herein are methods of treating insomnia by non-invasively applying hypothermal therapy to a subject's frontal cortex. The methods may include the steps of: positioning an applicator comprising a thermal transfer region in communication with the subject's skin over the prefrontal cortex; cooling the thermal transfer region to a first temperature consisting of the lowest temperature that may be tolerated by the subject without resulting in discomfort or arousal from sleep; maintaining the first temperature for a first time period extending at least 15 minutes prior to a target good night time; and maintaining a second temperature for a second time period extending at least 15 minutes after the target good night time.

In some variations, the first temperature is between about 10° C. and about 18° C. In some variations, the first temperature (the coolest tolerable temperature) corresponds to the coolest temperature that may be applied by the applicator when worn by the subject and not cause irritation (or arousal); this temperature may be empirically or experimentally determined. For example, the method may include a step of determining the first temperature for the subject.

The step of positioning the applicator may include securing the applicator in position. For example, the applicator may be held in position by straps. In some variations the applicator is adhesively secured. In general, the step of positioning the applicator may include securing the applicator over just the subject's forehead region. In some variations the applicator is limited to the forehead region.

In some variations the step of cooling the thermal transfer region to a first temperature comprises ramping (including gradually ramping) the temperature of the thermal transfer region from ambient temperature to the first temperature over at least five minutes, ten minutes, 15 minutes, etc.

The step of maintaining the first temperature may comprise holding the thermal transfer region at the first temperature for at least 30 minutes, one hour, etc.

In some variations the first temperature is the same temperature as the second temperature (e.g., between 10° C. and 18° C.). However, in some variations the method includes the step of changing the temperature of the thermal transfer region to the second temperature. In general, the second temperature may be a temperature between the first temperature and 30° C. For example, the second temperature may be between about 20° C. and about 25° C. The step of maintaining a second temperature for the second time may comprise maintaining the second temperature for more than one hour, 2 hours, 3 hours, 4 hours, 6 hours, 8 hours, or the entire sleep period. In some variations, the method further comprises adjusting the second temperature based on patient sleep-cycle feedback.

Also described herein are methods of treating insomnia by non-invasively applying hypothermal therapy to a subject's frontal cortex, the method comprising: positioning an applicator comprising a thermal transfer region in communication with the subject's skin over the prefrontal cortex; cooling the thermal transfer region to a first temperature consisting of the lowest temperature that may be tolerated by the subject without resulting in discomfort or arousal from sleep; maintaining the first temperature for at least 15 minutes prior to a target good night time; maintaining the first temperature for at least 30 minutes after the target good night time; and maintaining the temperature at a second temperature between the first temperature and 30° C. for at least 30 minutes.

Also described herein are methods of reducing sleep onset by non-invasively applying hypothermal therapy to a subject's frontal cortex, the method comprising: positioning an applicator comprising a thermal transfer region in communication with the subject's skin over the prefrontal cortex; cooling the thermal transfer region to a first temperature between about 10° C. and about 18° C.; and maintaining the first temperature for a first time period extending at least 15 minutes prior to a target good night time.

Also described herein are methods of sustaining sleep in a subject by non-invasively applying hypothermal therapy to the subject's frontal cortex, the method comprising: positioning an applicator comprising a thermal transfer region in communication with the subject's skin over the prefrontal cortex; after a target good night time, maintaining the thermal transfer region at a first temperature consisting of the lowest temperature that may be tolerated by the subject without resulting in discomfort or arousal from sleep; and maintaining the first temperature for a first time period extending at least 30 minutes after the target good night time. For example, the first temperature may be between about 10° C. and about 18° C.

In general the methods of treating insomnia (e.g., by decreasing sleep latency and/or by increasing sustained sleep may be performed by non-invasive cooling, and particularly by cooling the skin over the frontal cortex. In some variations, this cooling is limited to forehead region. The systems and devices described herein generally control the profile of the hypothermal therapy applied so that both the temperature and timing of the dosage is controlled. The system may be configured to apply complex dosing regimens and may be further configured to modify or select the dosing regimen based on feedback from the patient. Feedback may be patient selected (e.g., by adjusting or changing a control input) or may be based of one or more sensors detecting physiological parameters from the patient, such as sleep level, REM/NREM state, or the like.

As described in greater detail below the devices and systems for applying hypothermal therapy as described herein generally include an applicator (e.g., to be secured to or worn by the subject) having a thermal transfer region. The thermal transfer region is cooled. The thermal transfer region is also placed in contact with the skin over the subject's frontal cortex. In general, the applicator and thermal transfer region are configured so that the subject may comfortably and safely wear the device while sleeping or before sleeping (to increase drowsiness). The overall system may be configured to be quiet (so as not to disrupt sleep), and may include one or more controllers for regulating the temperature of the thermal transfer region, as mentioned above. The controller may be a microcontroller (including dedicated hardware, software, firmware, etc.). In some variations the system is configured to be worn by the subject every night, and thus may include a washable, disposable, or replaceable skin-contacting region. For example, the thermal transfer region may be covered by a disposable material or cover that can be replaced nightly with each use. In some variations one or more sensors may also be included to receive patient information and/or performance information on the system; this information may be provided to the controller and may be used to regulate the temperature. Overall, the system may be lightweight and easy to use.

Other features of the invention described herein are outlined below in greater detail, and with reference to the figures.

DETAILED DESCRIPTION

As describe above, it has been suggested that the restorative aspects of sleep can be linked regionally with heteromodal association cortex, especially in the frontal regions. The studies described herein clarify the regional cerebral metabolic correlates of this. In the first study, changes in regional cerebral metabolism that occur between waking and sleep in healthy subjects were identified. Fourteen healthy subjects (age range 21 to 49; 10 women and 4 men) underwent concurrent EEG sleep studies and [18F]fluoro-2-deoxy-D-glucose ([18F]-FDG) positron emission tomography (PET) scans during waking and NREM sleep. Whole brain glucose metabolism declined significantly from waking to NREM sleep. Relative decreases in regional metabolism from waking to NREM sleep were found in heteromodal frontal, parietal and temporal cortex, and in dorsomedial and anterior thalamus. These findings are consistent with a restorative role for NREM sleep largely in cortex that subserves essential executive function in waking conscious behavior. In the second study, changes in regional cerebral metabolism were identified that occur between usual NREM sleep and recovery NREM sleep following a night of sleep deprivation. In this study, homeostatic sleep need, or sleep drive, was modulated in a within-subjects design via sleep deprivation. Four young adult healthy male subjects (mean age+s.d.=24.9±1.2 years) received NREM sleep using [18F]fluoro-2-deoxy-D-glucose positron emission tomography ([18F]-FDG PET) assessments after a normal night of sleep and again after 36 hours of sleep deprivation. Both absolute and relative regional cerebral glucose metabolic data were obtained and analyzed. In relation to baseline NREM sleep, subjects' recovery NREM sleep was associated with: (1) increased slow wave activity (an electrophysiological marker of sleep drive); (2) global reductions in whole brain metabolism; and (3) relative reductions in glucose metabolism in broad regions of frontal cortex, with some extension into parietal and temporal cortex. The results demonstrate that the homeostatic recovery function of sleep following sleep deprivation is associated with global reductions in whole brain metabolism as well as greater relative reductions in broad regions of largely frontal, and related parietal and temporal cortex. In other words, sleep deprivation accentuates the decrease in brain metabolism normally seen during NREM sleep. Thus, a medical device that alters metabolism in a pattern similar to that seen in healthy sleep or recovery sleep following sleep deprivation may benefit insomnia patients.

Figure 1A:
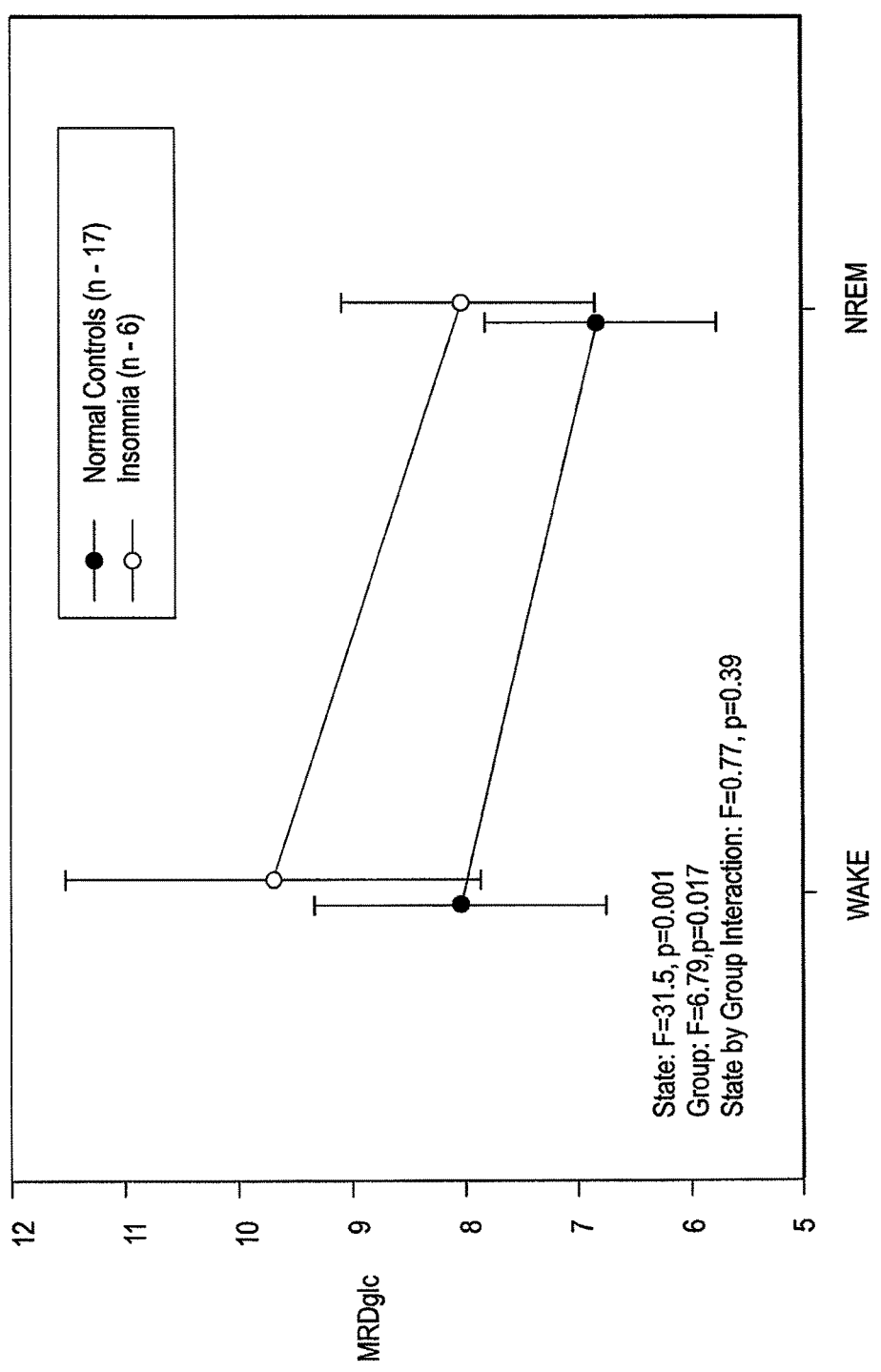
FIG. 1A is a graph illustrating the increase in whole brain metabolism in insomnia during waking and sleep.
Figure 1B:
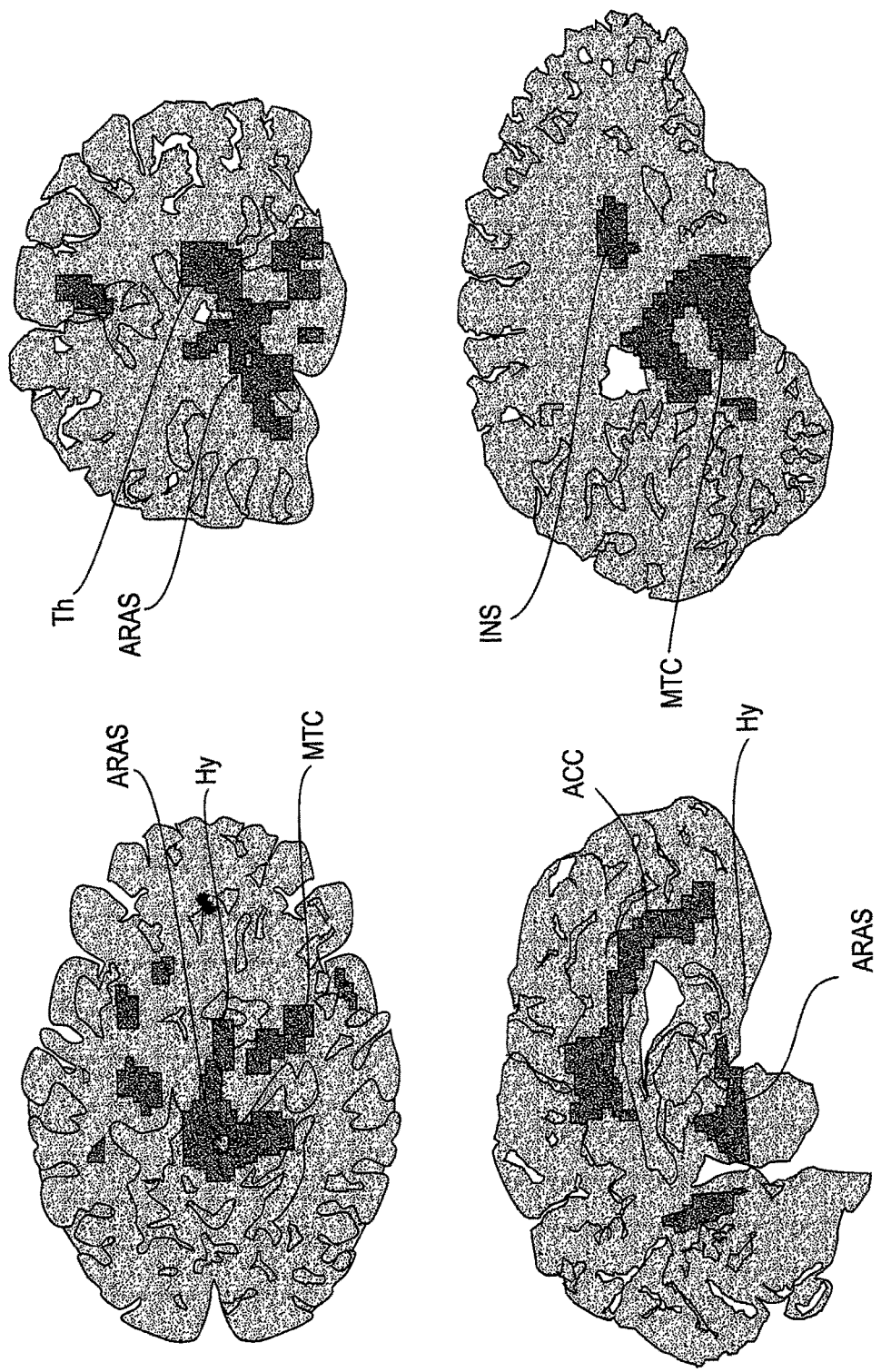
FIG. 1B illustrates brain regions where insomnia patients do not show as great of a decline in relative metabolism from waking to sleep.
Figure 1C:
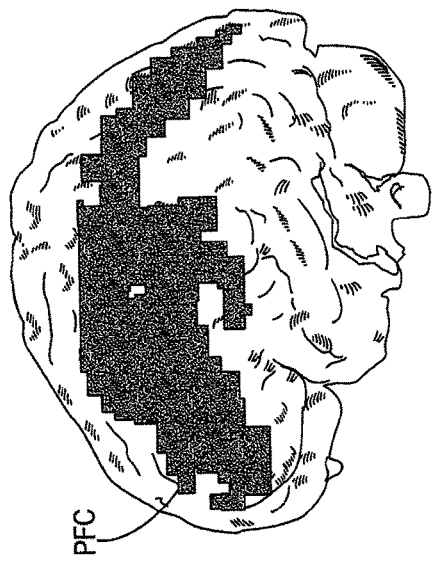
FIG. 1C shows brain regions where relative metabolism is decreased in insomnia patients.
Figure 1C:
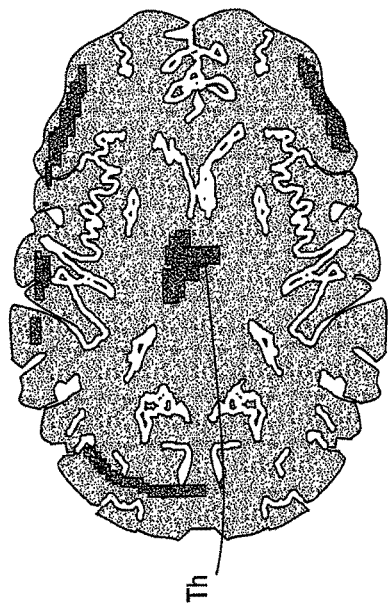
Figure 1C:
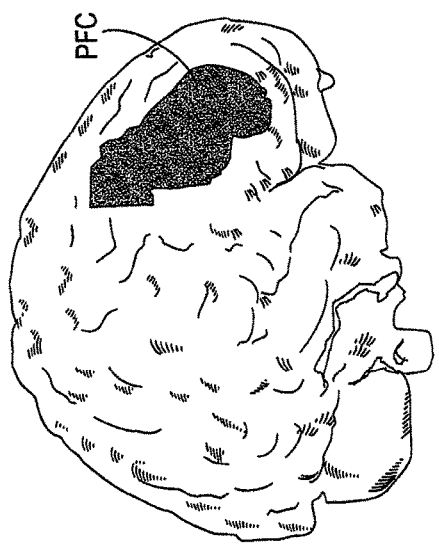
Figure 1C:
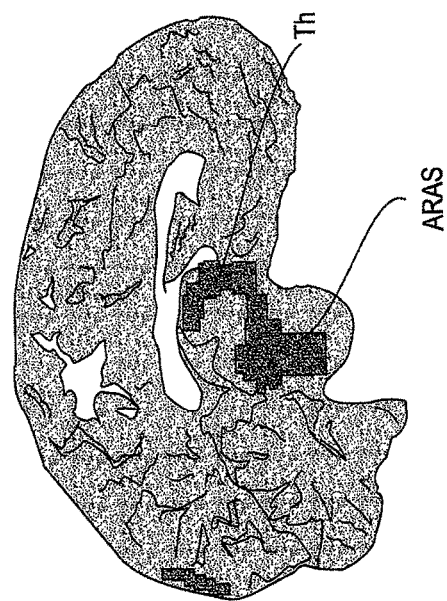

To test this hypothesis, a study of insomnia patients was performed to investigate how these normal changes in brain metabolism become disturbed in insomnia patients. Insomnia patients and healthy subjects completed regional cerebral glucose metabolic assessments during both waking and NREM sleep using [18F]fluoro-2-deoxy-D-glucose positron emission tomography (PET). Insomnia patients showed increased global cerebral glucose metabolism during sleep and wakefulness, as shown in FIG. 1A. A group x state interaction analysis confirmed that insomnia subjects showed a smaller decrease than did healthy subjects in relative metabolism from waking to NREM sleep in the ascending reticular activating system, hypothalamus, thalamus, insular cortex, amygdala and hippocampus and in the anterior cingulate and medial prefrontal cortices (as shown in FIGS. 1B and 1C). While awake, in relation to healthy subjects, insomnia subjects showed relative hypometabolism in a broad region of the frontal cortex bilaterally, left hemispheric superior temporal, parietal and occipital cortices, the thalamus, hypothalamus and brainstem reticular formation. This study demonstrated that subjectively disturbed sleep in insomnia patients is associated with increased brain metabolism. The inability of the insomniac patients to fall asleep may be related to a failure of arousal mechanisms to decline in activity from waking to sleep. Further, their daytime fatigue may reflect decreased activity in prefrontal cortex that results from inefficient sleep. These findings suggest interacting neural networks in the neurobiology of insomnia. These include a general arousal system (ascending reticular formation and hypothalamus), an emotion regulating system (hippocampus, amygdala and anterior cingulate cortex), and a cognitive system (prefrontal cortex). Notably, ascending arousal networks are functionally connected to cortical regions involved in cognitive arousal at the cortical level which can feedback and modulate more primitive brainstem and hypothalamic arousal centers. A medical device that alters metabolism in one or more portions of this network could benefit insomnia patients and produce more restful sleep.

A second study in insomnia patients was conducted to clarify the cerebral metabolic correlates of wakefulness after sleep onset (WASO) in primary insomnia patients testing the hypothesis that insomnia subjects with more WASO would demonstrate increased relative metabolism especially in the prefrontal cortex given the role of this region of the brain in restorative sleep and in cognitive arousal. Fifteen patients who met DSM-IV criteria for primary insomnia completed 1-week sleep diary (subjective) and polysomnographic (objective) assessments of WASO and regional cerebral glucose metabolic assessments during NREM sleep using [18F] fluoro-2-deoxy-D-glucose positron emission tomography (PET). Both subjective and objective WASO positively correlated with NREM sleep-related cerebral glucose metabolism in the pontine tegmentum and in thalamocortical networks in a frontal, anterior temporal, and anterior cingulate distribution. These effects may result from increased activity in arousal systems during sleep and/or to activity in higher order cognitive processes related to goal-directed behavior, conflict monitoring, emotional awareness, anxiety and fear. These processes are thought to be regulated by activity of the prefrontal cortex. A medical device that facilitates the normal reduction in relative metabolism in the prefrontal cortex during sleep could benefit insomnia patients.

As described above, cerebral hypothermia has been utilized in other medical disciplines as a means to reduce metabolic activity in the brain. Theoretical models suggest that application of a cooling stimulus at the scalp surface will cool and subsequently reduce metabolism in the underlying superficial cortex. These observations raised the possibility that a medical device that produced regional cooling to the scalp over the area of the prefrontal cortex, may reduce the hypermetabolism in that region in insomnia patients, allowing them to transition to sleep more easily and to subsequently obtain more restful sleep across the night. It is also conceivable that these cortical effects may have downstream effects on brainstem and hypothalamic centers of sleep/arousal regulation.

Figure 2A:
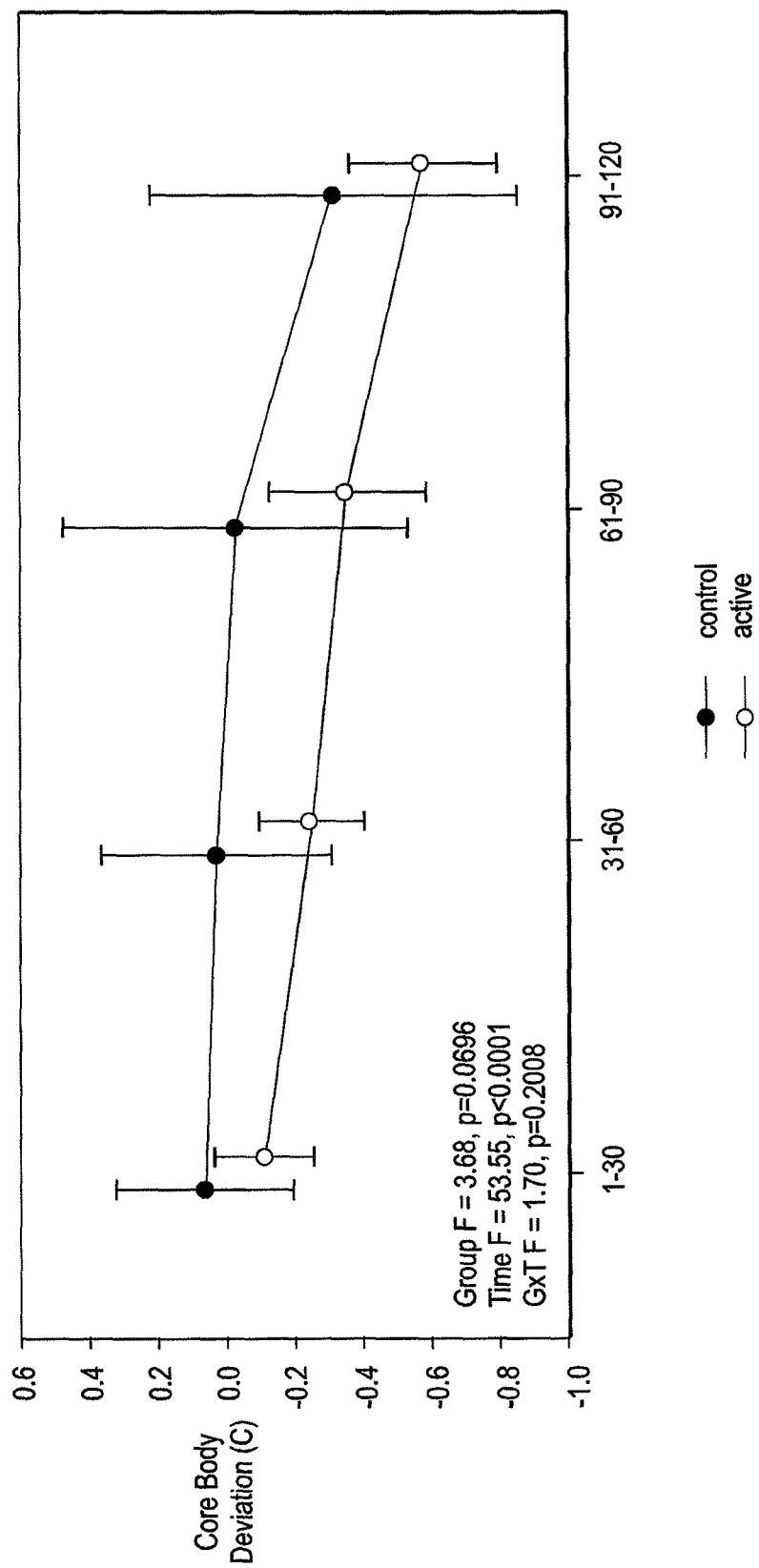
FIG. 2A is a graph illustrating change in the average core body temperature over time in patients treated and untreated using localized frontal hypothermia treatment.
Figure 2B:
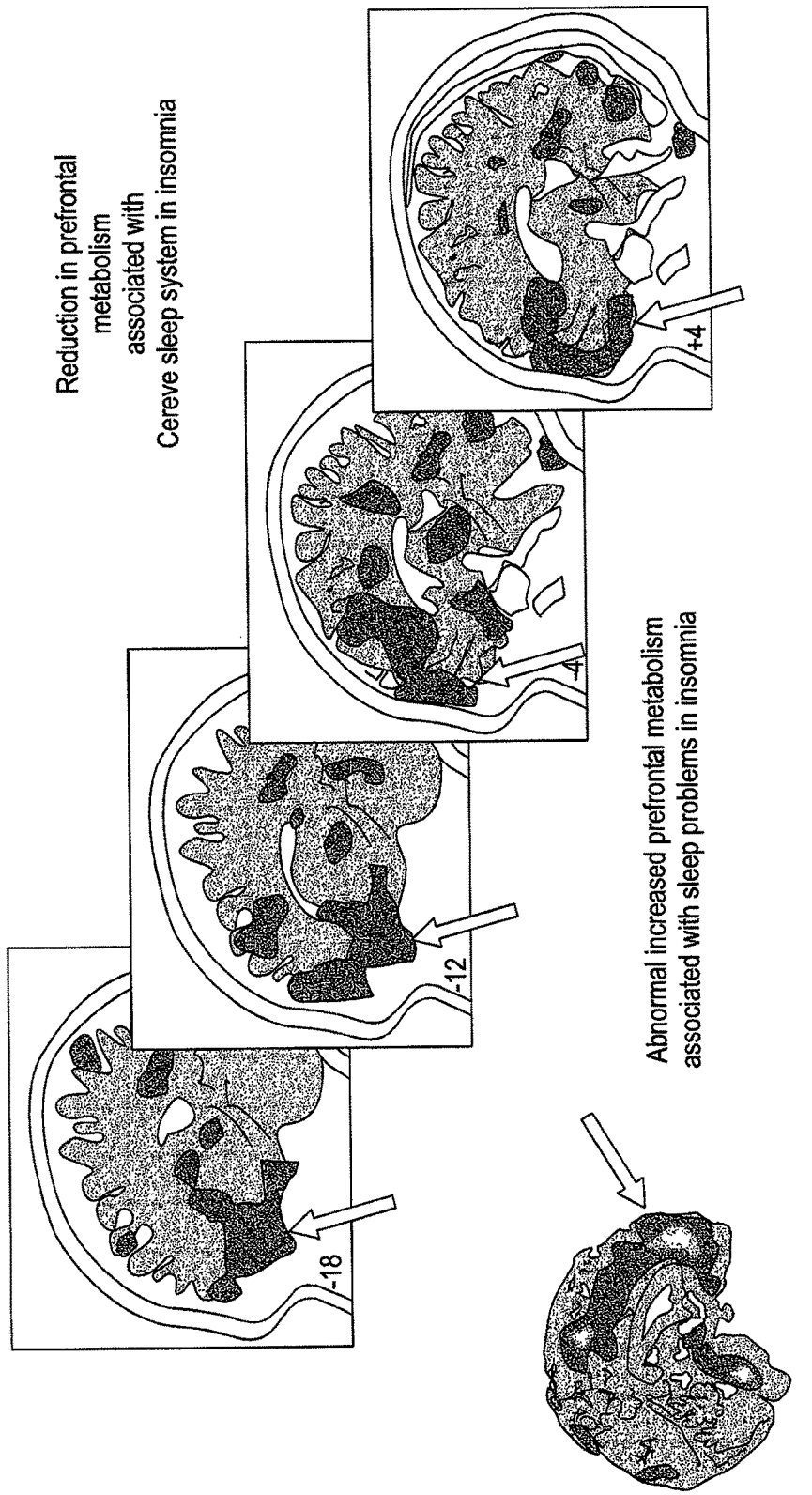
FIG. 2B shows PET scans of an insomniac patient undergoing treatment using frontal hypothermia and illustrating a reversal of prefrontal hypermetabolism.

A device was constructed to test the application of hypothermia applied to the skin over the prefrontal cortex as a method of treating insomnia and sleep-related phenomena. The device itself included a custom sized headpiece to fit the area of the scalp over the frontal cortex that circulated varying temperature fluids and a programmable cooling chamber/pump that provided the cooling and power for circulating the fluid to the headpiece. A study was performed to determine if the device lowered cerebral metabolism in the prefrontal cortex in insomnia patients. The study compared an active treatment (device at 14° C.) vs. a normothermic device comparison (control). Outcome measures included regional cerebral metabolism during sleep as measured by [18F]-FDG PET. 148 subjects were screened, 12 completed sleep studies, and 8 completed all PET imaging studies The data showed that the device reduced cerebral metabolism especially in the prefrontal cortex underneath the device. FIGS. 2A and 2B illustrate some of the findings, and show trends towards reductions in whole brain metabolism, reductions in relative regional metabolism (highlighted regions of FIG. 2B), especially in the prefrontal cortex, an increase in sleepiness and reduction in arousal while the device was worn for 60 minutes prior to bedtime, reductions in minutes of waking, increases in EEG delta spectral power and a reduction in core body temperature around the sleep onset period (FIG. 2A).

FIGS. 3A-3F illustrate some of the additional findings of this work. The study used to achieve these results and the design parameters for this study are described in greater detail below.

Significantly and surprisingly, 9 of 12 (75%) insomnia patients reported positive subjective effects of the device. All subjects encouraged further development of the device based on their experiences and all subjects easily understood/accepted the therapeutic concept for the treatment of their insomnia. They also reported: (1) a clear preference for the device over pills; (2) the device decreased distracting thoughts prior to getting in to bed; (3) the device facilitated sleep maintenance; (4) they experienced a subjective surprise that sleep passed without awareness; and (5) their sleep felt refreshing.

Figure 3C:
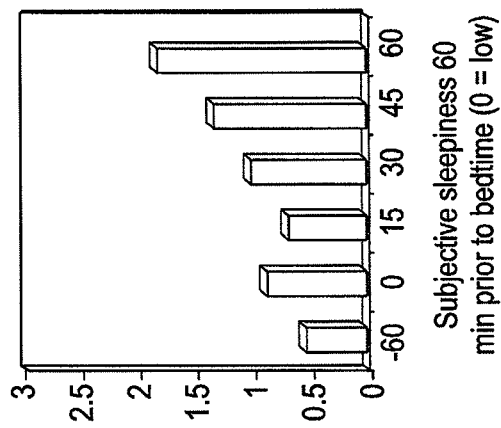
FIG. 3C shows a graph illustrating the increase in subjective sleepiness in insomniac patients treated with prefrontal hypothermia.
Figure 3B:
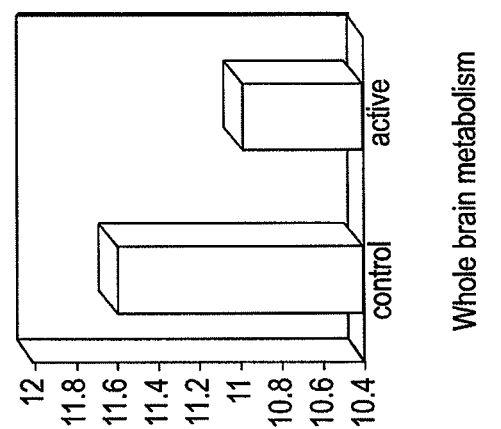
FIG. 3B shows a graph illustrating a decrease in whole brain metabolism (compared to control) in patients treated with prefrontal hypothermia.
Figure 3A:
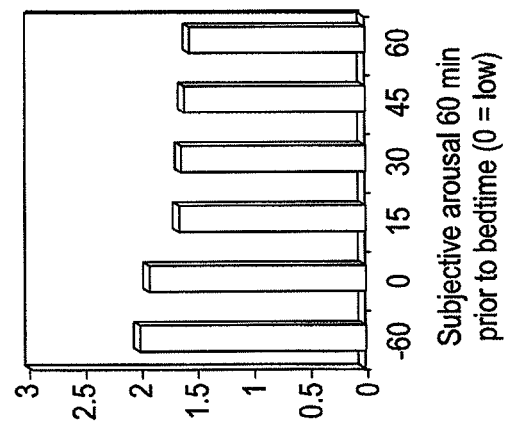
FIG. 3A shows a graph illustrating the decrease in subjective arousal in insomniac patients treated with prefrontal hypothermia as described herein.
Figure 3D:
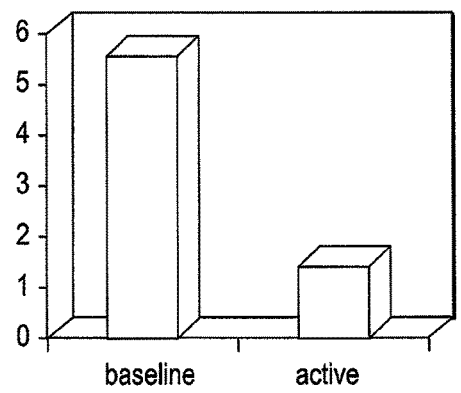
FIG. 3D shows a graph illustrating the decrease a reduction in waking after sleep onset in patients treated with prefrontal hypothermia.
Figure 3E:
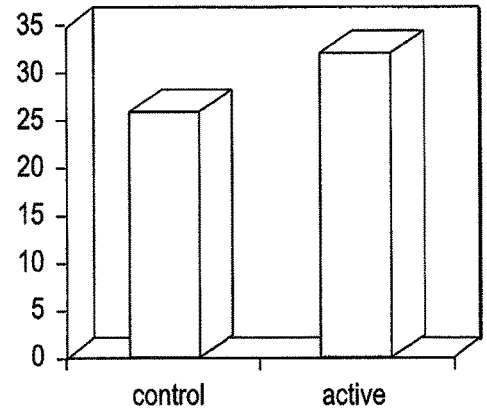
FIG. 3E is a graph illustrating an increase in delta power during sleep in patients treated with prefrontal hypothermia.
Figure 3F:
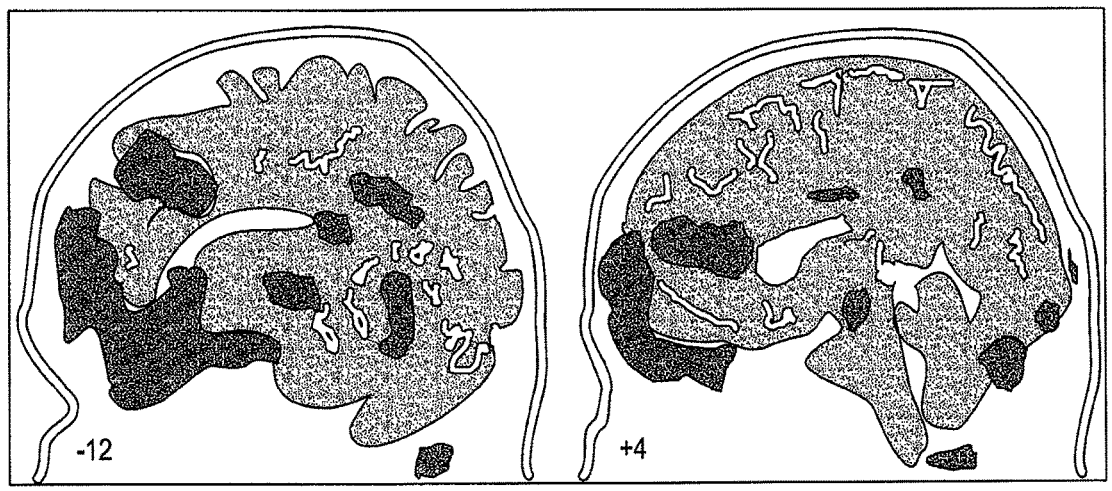
FIG. 3F is a side-by-side comparison of PET scans showing a reduction in regional metabolism in patients treated with prefrontal hypothermia.

As illustrated in FIG. 3A, the subjective arousal of patients treated with frontal/prefrontal hypothermia therapy decreased while wearing the device prior to getting into bed. In FIG. 3A, the x axis represents the 60 minute period prior to the subject getting into bed while wearing the device. The y-axis represents a subjective assessment of arousal (0=no arousal, 3=maximal arousal) measured in 15 minute increments up until the time that the patient got into bed. FIG. 3B shows a graph illustrating a decrease in whole brain metabolism measured by PET scans during NREM sleep between two conditions, an active condition (wearing the device at 14 degrees C. for 60 minutes prior to getting into bed and continuing during sleep until the time of measurement at 20-40 minutes following sleep onset) and a control condition (wearing the device at a thermoneutral 30 degrees C. for 60 minutes prior to getting into bed and continuing during sleep until the time of measurement at 20-40 minutes following sleep onset) in primary insomnia patients. FIG. 3C shows a graph illustrating the increase in subjective sleepiness in insomniac patients treated with prefrontal hypothermia. In FIG. 3C, the x axis represents the 60 minute period prior to the subject getting into bed while wearing the device. The y-axis represents a subjective assessment of sleepiness (0=no sleepiness, 3=maximal sleepiness) measured in 15 minute increments. FIG. 3D shows a graph illustrating the reduction in minutes of waking after sleep onset for the first 40 minutes of sleep during two conditions, an active condition (wearing the device at 14 degrees C. for 60 minutes prior to getting into bed and continuing during sleep for 40 minutes of measurement) and a control condition (wearing the device at a thermoneutral 30 degrees C. for 60 minutes prior to getting into bed and continuing during sleep for 40 minutes of measurement) in primary insomnia patients. FIG. 3E shows a graph illustrating the increase in automated EEG delta power (y-axis) during the first 40 minutes of NREM sleep between two conditions, an active condition (wearing the device at 14 degrees C. for 60 minutes prior to getting into bed and continuing during sleep until the end time of measurement at 40 minutes) and a control condition (wearing the device at a thermoneutral 30 degrees C. for 60 minutes prior to getting into bed and continuing during sleep until the end time of measurement at 40 minutes) in primary insomnia patients. FIG. 3F shows the results of a comparison of regional cerebral metabolism during NREM sleep between two conditions, an active condition (wearing the device at 14 degrees C. for 60 minutes prior to getting into bed and continuing during sleep until the time of PET measurement at 20-40 minutes following sleep onset) and a control condition (wearing the device at a thermoneutral 30 degrees C. for 60 minutes prior to getting into bed and continuing during sleep until the time of PET measurement at 20-40 minutes following sleep onset) in primary insomnia patients. The brain regions highlighted in blue on two different sections through the brain show the areas of the brain, especially in the frontal cortex in the area underneath the device placement, where metabolism was significantly decreased in the active condition vs. the control condition.

Further studies were performed to determine the tolerability and efficacy of a medical device that delivers frontal hypothermia for an extended period (e.g., all night) for the treatment of insomnia. These studies were also performed to further define the specific thermal energy transfer parameters associated with treatment efficacy.

Figure 4A:
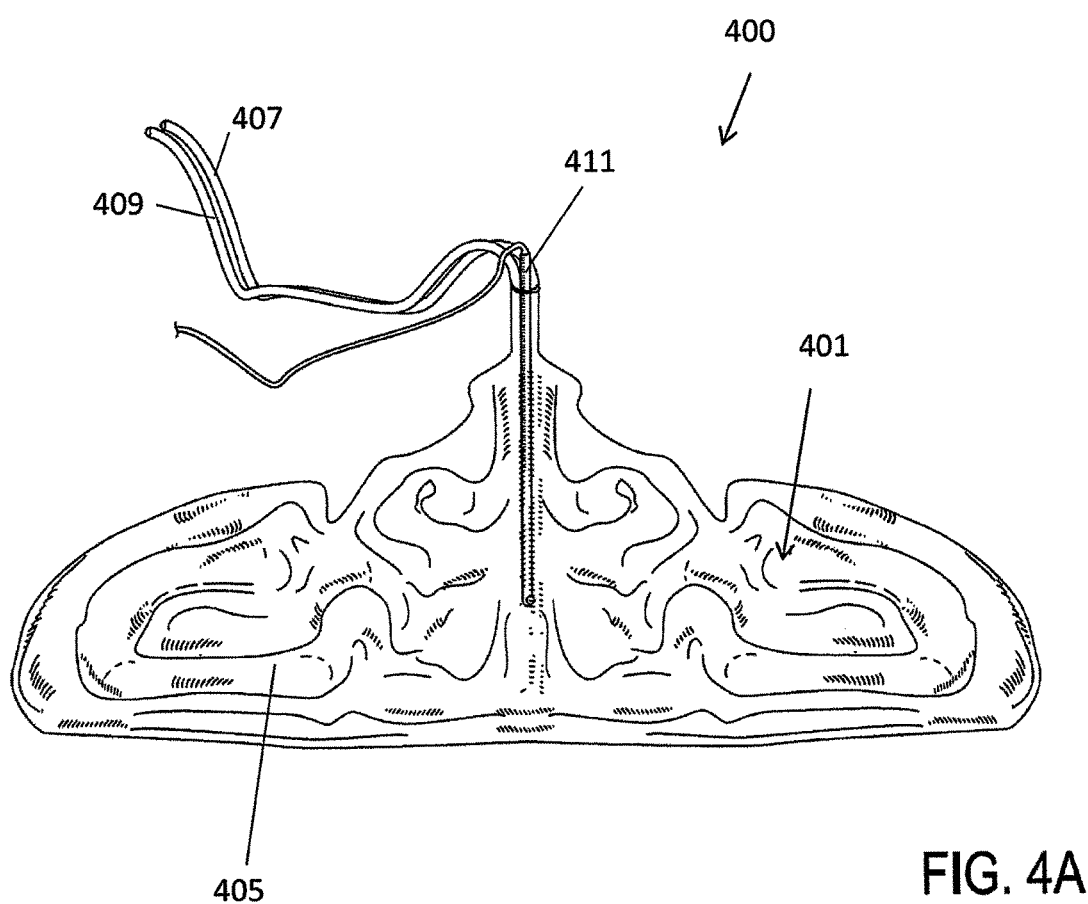
FIG. 4A shows one variation of a headpiece of a device for applying hypothermia.
Figure 4B:
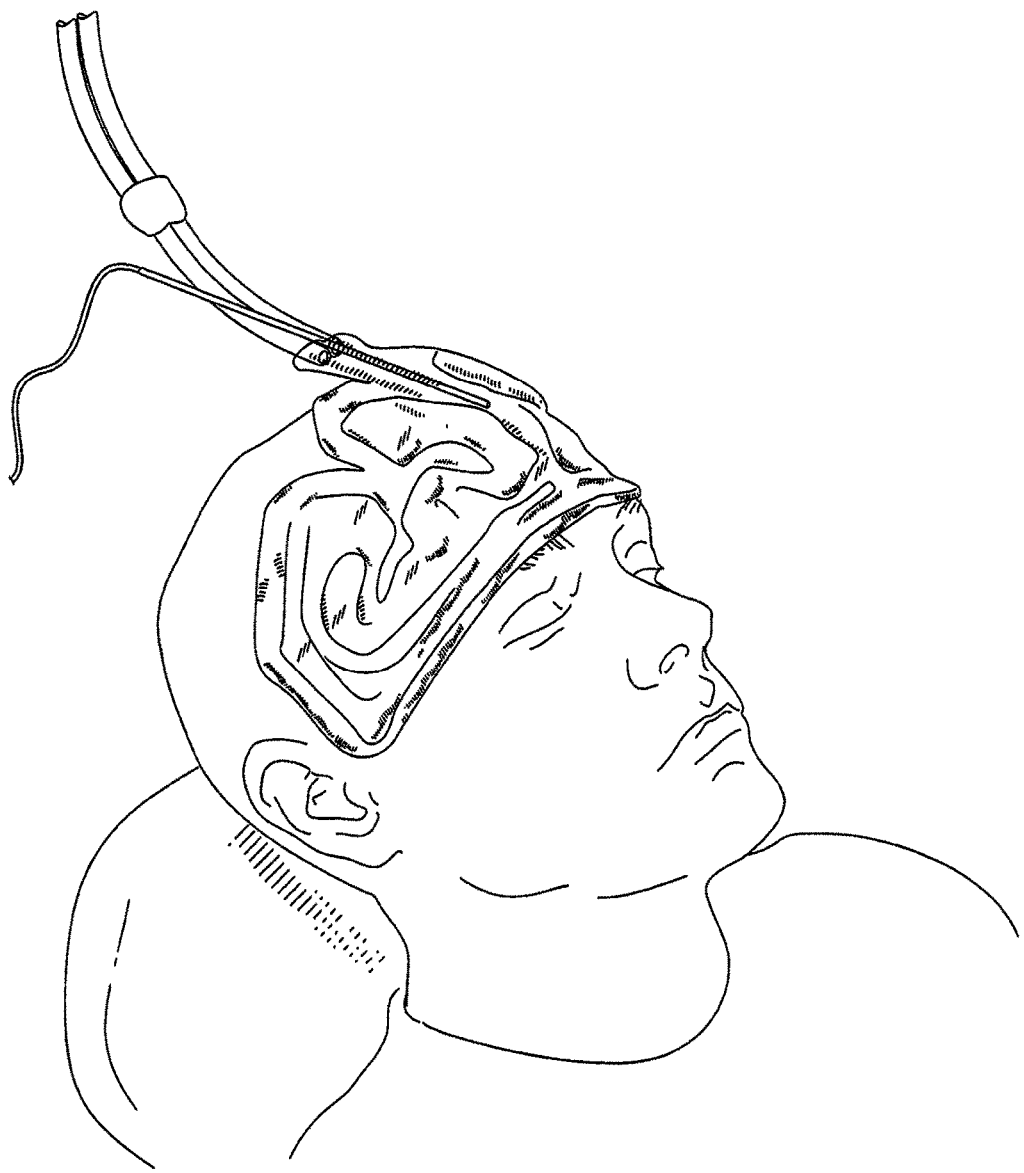
FIG. 4B illustrates the headpiece applied to a subject's head.

Data comparing subjective and objective measures of sleep, and tolerability in mid-life insomnia patients across 4 frontal hypothermia intervention conditions were collected. These included two active and one neutral "doses" of frontal hypothermia device temperature settings and a no device control as follows: (1) a "no device" control; (2) a device at "thermo-neutral" 30° C. and flow rate of 7 gallons per hour; (3) a device at 22° C. and flow rate of 7 gallons per hour; and (4) a device at 14° C. and flow rate of 7 gallons per hour. Based on the flow rates of the active doses, thermal energy will be drawn off of the forehead at a thermal transfer rate ranging from 10-25 W (power). The surface area of the applicator for the experimental device (e.g., the headpiece) is shown in FIGS. 4A and 4B.

Twelve insomnia patients were entered into this study. Each intervention was applied for two nights' duration, separated by at least 2 nights non-intervention sleep at home. The order of presentation of conditions was randomized across subjects in order to control for adaptation and carry over effects from one condition to the next. Primary inclusion criteria included DSM-IV diagnosis of primary insomnia; ages 18-65 (age range minimizes effects of aging on sleep and regional cerebral metabolism that could confound interpretation of studies while encompassing the most prevalent ages for insomnia). Subjects remained alcohol-free and avoided drugs that could affect sleep. Insomnia was defined according to the "General Insomnia Criteria" set forth in the International Classification of Sleep Disorders, 2nd Edition and the criteria for "Insomnia Disorder" in the Research Diagnostic Criteria for Insomnia. These criteria require: (1) a complaint of difficulty falling asleep, staying asleep, awakening too early, or nonrestorative sleep; (2) adequate opportunity for sleep; and (3) evidence for at least one type of daytime impairment related to the sleep complaint. By setting a minimum duration criterion of at least one month and requiring the sleep complaints to be present on most days, we were also consistent with criteria for "Primary Insomnia" in the Diagnostic and Statistical Manual of Mental Disorders, 4th Edition. In order to insure a minimum level of overall severity and comparability with other published data, we required that insomnia participants score >14 on the Insomnia Severity Index. Further, we required that their screening and baseline sleep diaries demonstrate wakefulness after sleep onset of >30 minutes and sleep efficiency <85% on at least 50% of nights, which is consistent with the diagnostic criteria above, and with recommendations for quantitative insomnia criteria.

Primary exclusion criteria included neuropsychiatric disorders that may independently affect sleep, brain function or cognition, such as current major syndromal psychiatric disorders, including DSM-IV mood, anxiety, psychotic, and substance use disorders. Specific exclusionary diagnoses included major depressive disorder, dysthymic disorder, bipolar disorder, panic disorder, obsessive complusive disorder, generalized anxiety disorder, any psychotic disorder, and any current substance use disorder. Subjects were not excluded for subsyndromal symptoms or disorders in these domains (e.g., minor depression, limited symptom panic attacks). We did not exclude subjects for simple phobia, social phobia, past eating or substance use disorders, specific learning disabilities, or personality disorders. Psychiatric disorders were evaluated using the Structured Clinical Interview for DSM-IV (SCID). Other exclusion criteria include: unstable medical conditions including severe cardiac, liver, kidney, endocrine (e.g. diabetes), hematologic (e.g. porphyria or any bleeding abnormalities), other impairing or unstable medical conditions or impending surgery, central nervous system disorders (e.g., head injury, seizure disorder, multiple sclerosis, tumor), active peptic ulcer disease, inflammatory bowel disease, and arthritis. Individuals with well-controlled health conditions that do not affect sleep or well-being (e.g., well-controlled thyroid disorders, asthma, or ulcer) were not excluded. We excluded women who were pregnant, nursing, or sexually active but not using an effective method of birth control. Subjects who met inclusion criteria and did not have any specific exclusion criteria also had a complete medical history and physical examination, conducted by a physician's assistant, and a set of routine laboratory tests to rule out any unsuspected medical conditions. Specific tests included fasting glucose, complete blood count, liver function tests, serum chemistry, thyroid function tests, urinalysis, and urine drug screen to examine surreptitious sedative use. Other exclusion criteria included: irregular sleep schedules; an AHI (apnea hypopnea index) >20 and oxyhemoglobin desaturations <90% for at least 10% of the night from a diagnostic sleep study; use of medications known to affect sleep or wake function (e.g., hypnotics, benzodiazepines, antidepressants, anxiolytics, antipsychotics, antihistamines, decongestants, beta blockers, corticosteroids); or consumption of more than one alcoholic drink per day, or more than 7 drinks per week.

Subjects were asked to report to the sleep laboratory about 2-3 hours prior to their usual good night time (GNT) for 2 consecutive nights on 4 separate occasions, each separated by at least 2 days. After being studied throughout the night on each night, subjects were allowed to leave the sleep lab after awakening each morning until returning the following evening. On arrival at the sleep lab, subjects were prepared for their studies as follows. Subjects first ingested a temperature monitoring pill (described below) along with their last drinks of fluid. Subjects will remain n.p.o. for the next 3 hours, then allowed water on a p.r.n. basis for the remainder of the study. They were fitted with a belt pack that included a monitoring device to receive the signal from the pill. Subjects were fitted with electrodes and thermistors for monitoring polysomnography, EKG and skin temperature as described below. About 60 minutes prior to good night time (GNT), subjects were seated in a comfortable chair in a sleep lab bedroom. At that time, they filled out questionnaires and rating scales (described below). From the end of completion of questionnaires until 45 minutes prior to GNT (GNT for subjects in the no device condition), technicians ensured that all recording equipment was registering appropriate signals, then at 45 minutes prior to GNT (except for the no device condition), they applied the temperature controlling forehead pad (described below) at a temperature of 30 degrees Celsius (normothermia). After application of the temperature controlling forehead pad, the technician then set the water bath temperature to the desired endpoint for that night's study (14, or 22 or 30 degrees Celsius) where it remained for the remainder of the night of sleep. Equilibration to the desired temperature occurred after 10-15 minutes. Subjects completed rating scales as defined below after the device had been applied, then every 15 minutes until GNT. After completion of the last rating scales at GNT, subjects were asked to get in to bed to sleep undisturbed with monitoring electrodes and thermistors in place for the remainder of the night until their habitual good morning time (GMT). At that time, recording devices and the frontal hypothermia device were removed, morning questionnaires including post-sleep evaluations and subjects were free to leave for the day until returning for the next night's study.

Temperature doses were randomized for the study. The water bath temperatures on the three device interventions included: 14, 22 and 30° Celsius. The flow rate through the mask was 7 gallons per hour at the thermal transfer rate ranging from 10-25 W (power). The lower temperature (about 14° C.) was determined as the limit to which a cold stimulus is experienced by subjects to be cold, yet not uncomfortably cold to the point of producing discomfort. The 30° C. temperature was chosen as a temperature experienced by subjects as "neutral", i.e. not cool or warm, and the 22° C. temperature was chosen as halfway between these two to provide one additional temperature range. To eliminate any order effects of application, the ordering of the three temperature conditions of the frontal hypothermia water bath and the no device condition was randomized across subjects. Preliminary studies show these ranges of temperatures to be well tolerated and without adverse events.

Polysomnography was monitored while frontal hypothermia or no device was applied on each night in the sleep lab. EEG sleep was monitored across the night while subjects slept from GNT to GMT to assess effects of different temperature levels of frontal hypothermia on measures of sleep latency, sleep maintenance and delta EEG spectral power during subsequent sleep. The polysomnographic EEG montage for all these purposes consisted of a single EEG channel (C4/A1-A2), bilateral EOGs referenced to A1-A2, and bipolar submental EMG. Manual and automated scoring of the EEG was performed with emphasis on EEG spectral power in the theta and delta frequency bands as measures of arousal and depth of sleep.

The sleep montage on a sleep disorder screening night conducted prior to any other night of sleep, consisted of a single EEG channel (C4/A1-A2), bilateral EOGs referenced to A1-A2, bipolar submental EMG (electromyogram), single-lead EKG (electrocardiogram), and anterior tibialis EMG. Nasal airflow was monitored by the nasal pressure transducer technique consisting of a standard nasal cannula for $O_2$ delivery, but instead of being attached to an $O_2$ source, it was attached to a pressure transducer to detect pressure swings at the nasal opening. Oral airflow was recorded using a thermistor positioned in front of the mouth. Breathing effort was recorded by respiratory inductance plethysmography (R.I.P.) which employed two elasticized bands, one around the rib cage and one around the abdomen, each containing an embedded wire coil. As the circumference of the two chest wall "compartments" change with breathing effort, the embedded wires are stretched and a signal is generated. $SpO_2$ was non-invasively recorded in the standard fashion by pulse oximetry (Ohmeda, Biox 3700 at fastest possible response time).

Visual sleep stage scoring was also performed. Inter-rater reliability of visual sleep stage scoring was conducted quarterly by the laboratory manager to ensure that technologists maintain consistency over time. Epoch-by-epoch agreement in sleep staging was measured monthly and characterized by Fleiss' modified kappa statistic, intraclass correlations, and absolute % agreement in epochs. Kappa values for REM and wakefulness have values >80, intraclass correlations are >0.85, and % agreement >90%. The following visually scored sleep measures were obtained: sleep latency; time spent asleep; and sleep efficiency.

Sleep latency (SL) is the interval between Good Night Time (GNT) and the first epoch of 10 consecutive minutes of Stage 2-4 NREM or REM sleep, interrupted by no more than one minute of wakefulness. It is expressed in minutes. Time spent asleep (TSA) is the total time spent in any stage of NREM or REM sleep after sleep onset. It is expressed in minutes. Sleep efficiency (SE) is the ratio of time spent asleep to total recording period duration, multiplied by 100. It is expressed as a percentage (SE=[TSA/TRP]×100).

Power spectral analysis was used to quantify the frequency content of the sleep EEG from 0.25-50 Hz. Software was developed in-house to perform spectral analysis of the sleep EEG. Modified periodograms are computed using the Fast Fourier transform (FFT) of non-overlapping 4-second epochs of the sleep EEG. One-minute EEG spectra are obtained as the average of the artifact-free 4-second spectra for a given minute. These 1-minute spectra are time-aligned with the hand scores to allow for the computation of average spectra for various time intervals (e.g., the first NREM period). To further reduce the data for statistical analysis, the spectra can be banded as desired (e.g., a 0.5-4 Hz delta band). This software includes an automated detection routine to eliminate high frequency (predominantly muscle) artifacts (Brunner et al., 1996). Signal processing using power spectral analysis was completed. Power spectral analysis was used quantify EEG power across the frequency range. Power in the delta band was used as dependent measures across studies in the program as a whole. For example, delta power is thought to reflect the homeostatic sleep drive that increases exponentially as a function of prior wakefulness, decreases exponentially during the course of NREM sleep episodes, and is reduced as a function of aging and numerous sleep disorders. Delta power is expressed as microV$^2$/Hz in the 0.25-4.0 Hz frequency range during NREM sleep.

The temperature applicator (the headpiece) in this example is temperature-regulated by control of the temperature of a circulating fluid ($H_2O$ in this example). The temperature of the internal fluid was monitored and regulated in water bath connected by tubing to the headpiece. The temperature was monitored by the water bath and converted to a signal recorded on the polygraph.

Subject temperature was measured in part by a temperature assessing pill (Vitalsense® system) that was swallowed to record continuous core body temperature over the nights of study in the sleep lab. The pill used a tiny radio transmitter to measure core body temperature and sent the information to a belt pack worn by the subject. The pill passed through the subject undigested and was then discarded with a bowel movement. The device has been approved as safe by the U.S. Food and Drug Administration (FDA) [510(k) number K033534]. Each night, the system was checked for an active signal signifying that the pill had not been passed. If no signal was detected, a new pill was initiated and swallowed. Thermistors were also used to record skin temperature before and during application of frontal hypothermia at: (1) frontal scalp underneath the pad; (2) occipital scalp; and (3) back of non-dominant hand. Thermistors measured ambient room temperature before and during the application of frontal hypothermia.

As mentioned, in this study the device for applying frontal hypothermia included a temperature-controlling device specifically designed for this application for applying frontal hypothermia. The custom cooling apparatus circulated temperature controlled water, pumped from a water bath to a pad on the patient's forehead. The pad is custom shaped from two laminated sheets of vinyl to cover the target area on the forehead overlaying the prefrontal cortex. The remainder of the head remained uncovered except for a thin nylon spandex cap to retain the pad and hold the tubing. In this exemplary system, a thin layer of hydrogel between the skin and pad improved thermal conductivity and kept the pad against the forehead with minimal air gaps.

The device used in this study included a circulating programmable laboratory water bath (e.g., Polyscience: Polyscience Programmable Model 9112). The system was programmable. The headpiece included a custom shaped vinyl laminate produced with a prescribed flow pattern (e.g., see FIG. 4A) and a boundary matching the surface area of the head targeted for cooling. A hydrogel adhesive may be used to hold the pad snugly against the forehead without applying excessive pressure to the pad. An adhesive may also increased the surface area for contact and provided a high efficiency thermal transfer surface.

In this example, the temperature applicator of the headpiece 400 was used with a retainer device (not shown) to hold the temperature applicator against the subject's head. This head holder in this example was a thin nylon spandex cap that was placed over the laminate to keep it positioned on the head before and during sleep. The applicator 400 includes a thermal transfer region (surface 402) which is configured to be worn against the patient's forehead. As mentioned, an adhesive (e.g., hydrogel, not shown) may be included to help form a thermal contact with the forehead. The applicator 400 shown in FIG. 4 includes channels 405, through which cooled (cooling) thermal transfer fluid may be moved; in this example an inlet 407 and outlet 709 may be included to pump thermal transfer fluid through the applicator. In this example, the applicator also includes at least one sensor 411 comprising a thermister for monitoring the temperature of the applicator; this information may be fed back to the system for regulating the temperature of the applicator.

The analyses tested differences in sleep between insomniacs and non-insomniacs over a range of active and control temperatures of frontal hypothermia in a within-subjects design presented in a randomized order. The major group difference that was analyzed was the within-subject intervention study comparing the insomnia patients across the various interventions. Multivariate analysis of covariance is an omnibus approach used to compare multiple measures between groups while controlling for known covariates such as age and gender. A repeated domain was added to the model to explore differences in measures across interventions. The results tested whether there is a linear effect from baseline to neutral temperature to 22° C. to 14° C. temperature of the circulating water at identical flow rates and using identical thermal transfer pad over the forehead. Age- and gender-matched historical control subjects' data are shown on the graphical results displayed in FIGS. 5A-5L to illustrate relationships to normative sleep.

For the 12 primary insomnia subjects examined (9 women/3 men, with a mean age+s.d. of 44.62+12.5 years) compared to 12 healthy age- and gender-matched historical control subjects, the results show a remarkable effect on hypothermic treatment, particularly at lower temperatures (closer to the 14° C. parameter). The graphs shown in FIGS. 5A-5L also provide a comparison in relation to normative measures for healthy control subjects studied in the same laboratory environment.

These results show that that the thermal effect (the hypothermic effect) applied non-invasively to the subject's skin adjacent to the prefrontal cortex has a temperature-dependent effect. This effect may also be time-dependent, in applying the therapy for a time before the GNT and for some period after GNT, including the entire night or a portion of the night during sleep. The effects and parameters are illustrated below.

Figure 5A:
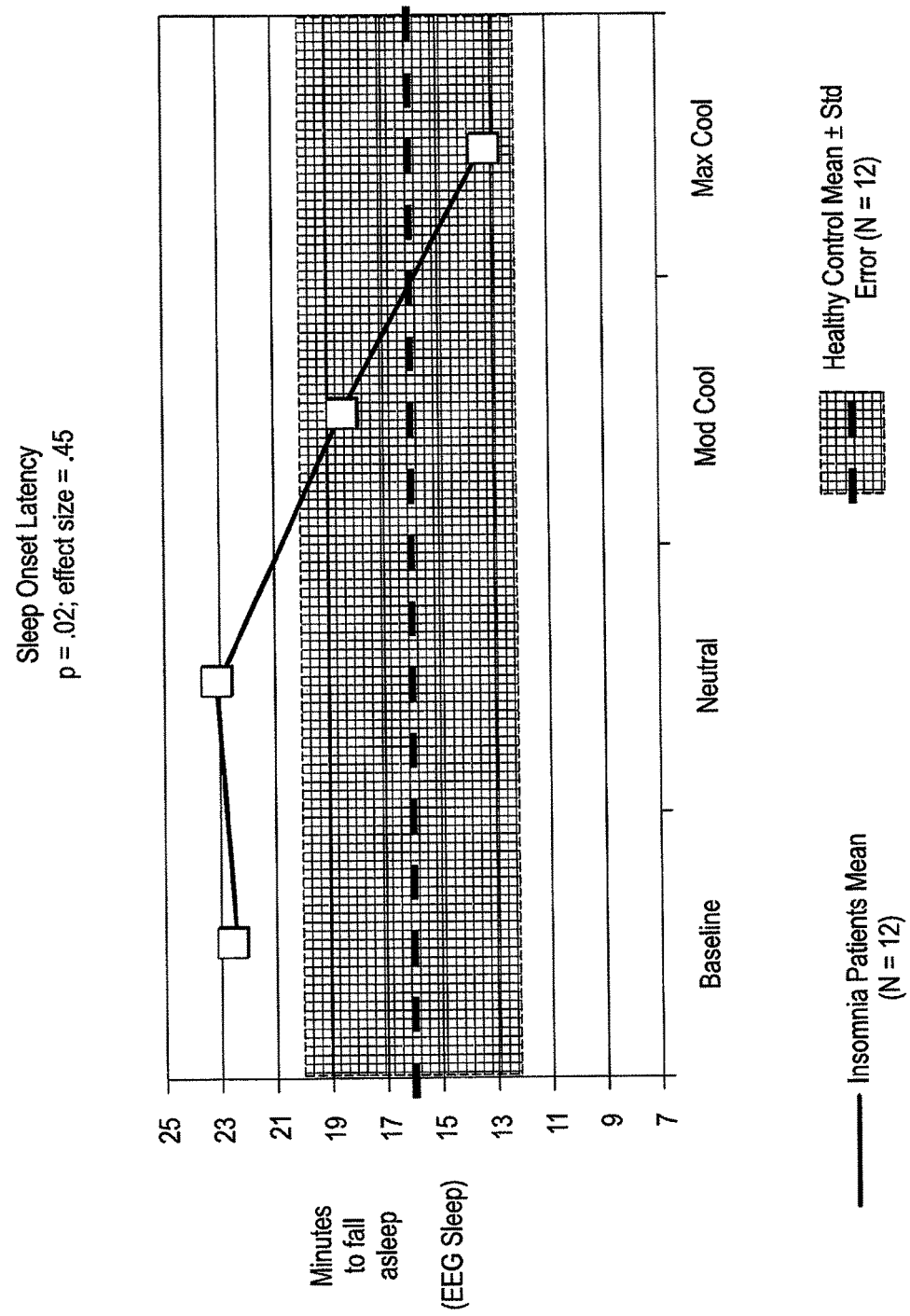
FIG. 5A shows the effect of one variation of a device for applying prefrontal hypothermia on sleep onset latency in an insomniac patient compared to non-insomniac.
Figure 5B:
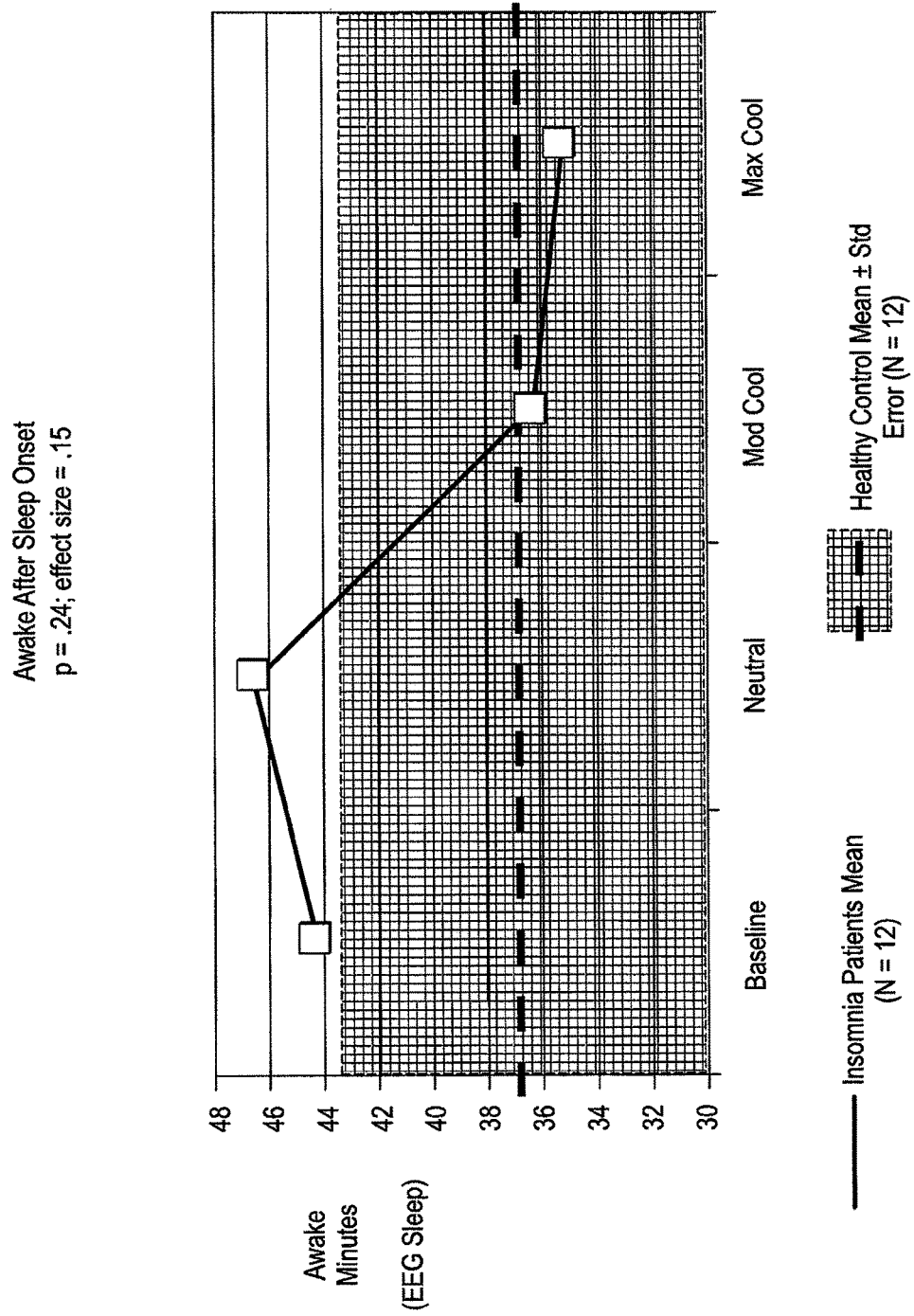
FIG. 5B shows the effect of one variation of a device for applying prefrontal hypothermia on awake after sleep onset in an insomniac patient compared to non-insomniac.

For example, the system typically applies (non-invasively) hypothermic therapy to a patient's skin above (adjacent) to the prefrontal cortex for an extended period of time at a temperature that is not perceived as uncomfortably cold (e.g., typically greater than or about 10° C., such as 14° C.). This therapy typically shortens the time to fall asleep, as illustrated in FIG. 5A. In FIG. 5A the sleep onset latency of insomniac patients experiencing cooling (both moderate cooling at 22° C. and maximum cooling at 14° C.) was significantly shorter than in untreated subjects. This effect was also seen to be temperature dependent; greater cooling ("max cool") at 14° C. had a more rapid sleep onset.

Figure 5C:
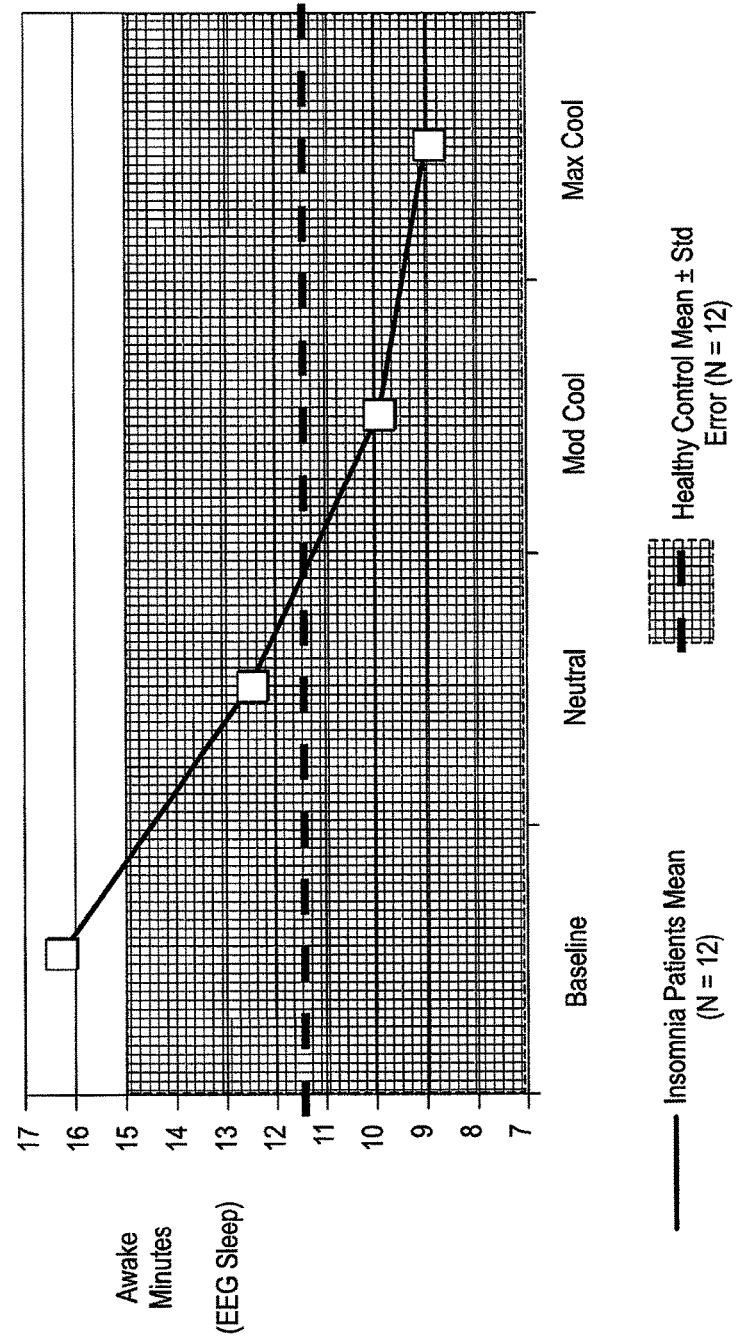
FIG. 5C shows the effect of one variation of a device for applying prefrontal hypothermia on wakefulness in the first half of the night in an insomniac patient compared to non-insomniac.
Figure 5D:
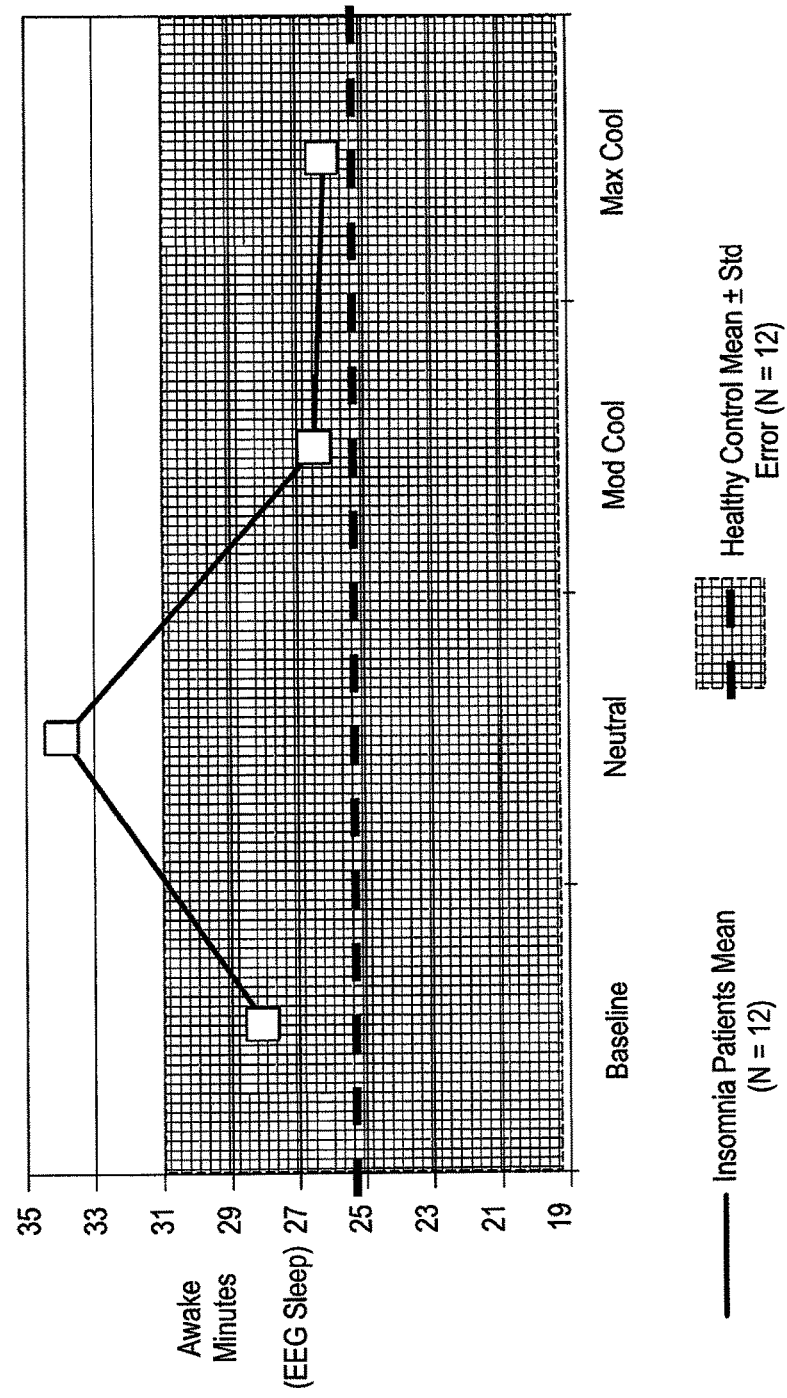
FIG. 5D shows the effect of one variation of a device for applying prefrontal hypothermia on wakefulness in the second half of the night in an insomniac patient compared to non-insomniac.

In addition to helping the insomniac patient fall asleep more quickly, the system also enhanced and increased the duration of sleep, as shown in FIGS. 5B-5E, an effect which was also temperature dependent. For example, hypothermic treatment also diminished wakefulness after sleep onset; in FIGS. 5B, 5C and 5D, the time the insomniac patient was awake after onset of sleep fell to within normal controls, particularly in the first half of the night, as shown in FIG. 5C. Although this preliminary work is not definitive with respect to the effect in the first half of the night compared to the second half, it suggests that it may be sufficiently effective to provide hypothermic treatment for at least the first half of the night (e.g., anticipated sleep period). For example, for between about 2-6 hours, and less effective beyond that point. Alternatively, it may be beneficial to shift the temperature applied either up or down, later during sleep in order to further regulate the patient's sleep.

Figure 5E:
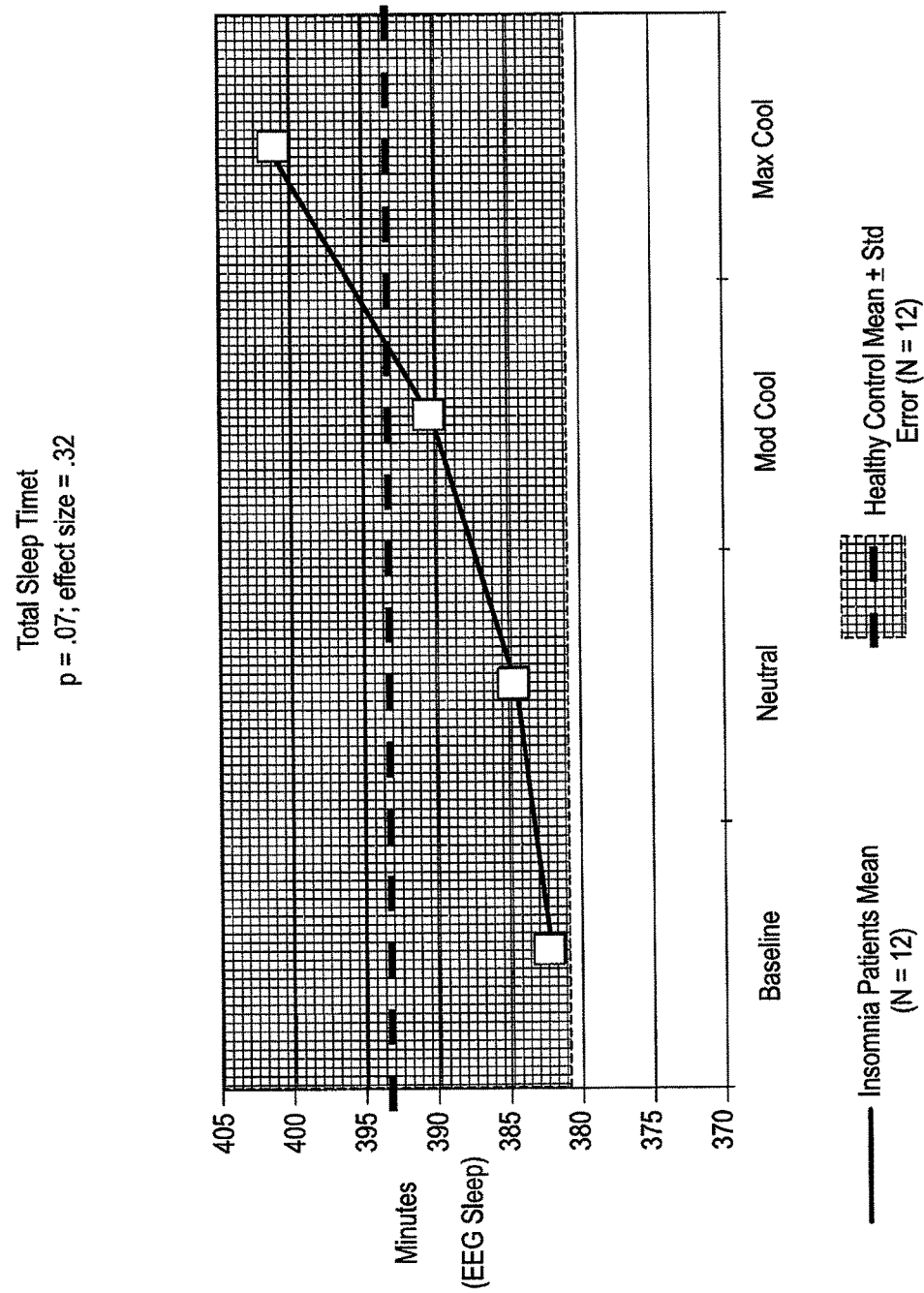
FIG. 5E shows the effect of one variation of a device for applying prefrontal hypothermia on total sleep time in an insomniac patient compared to non-insomniac.
Figure 5F:
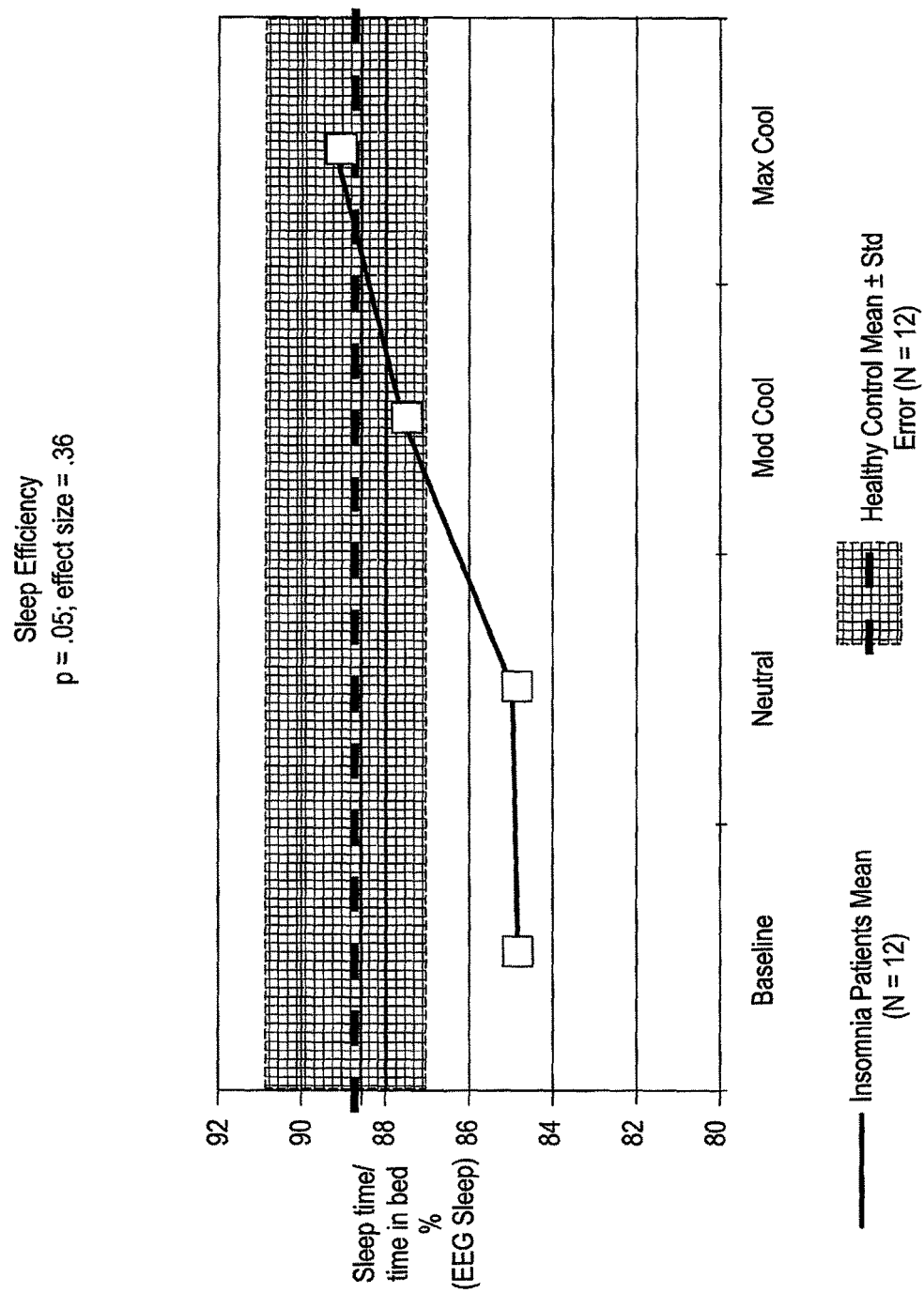
FIG. 5F shows the effect of one variation of a device for applying prefrontal hypothermia on sleep efficiency in an insomniac patient compared to non-insomniac.
Figure 5G:
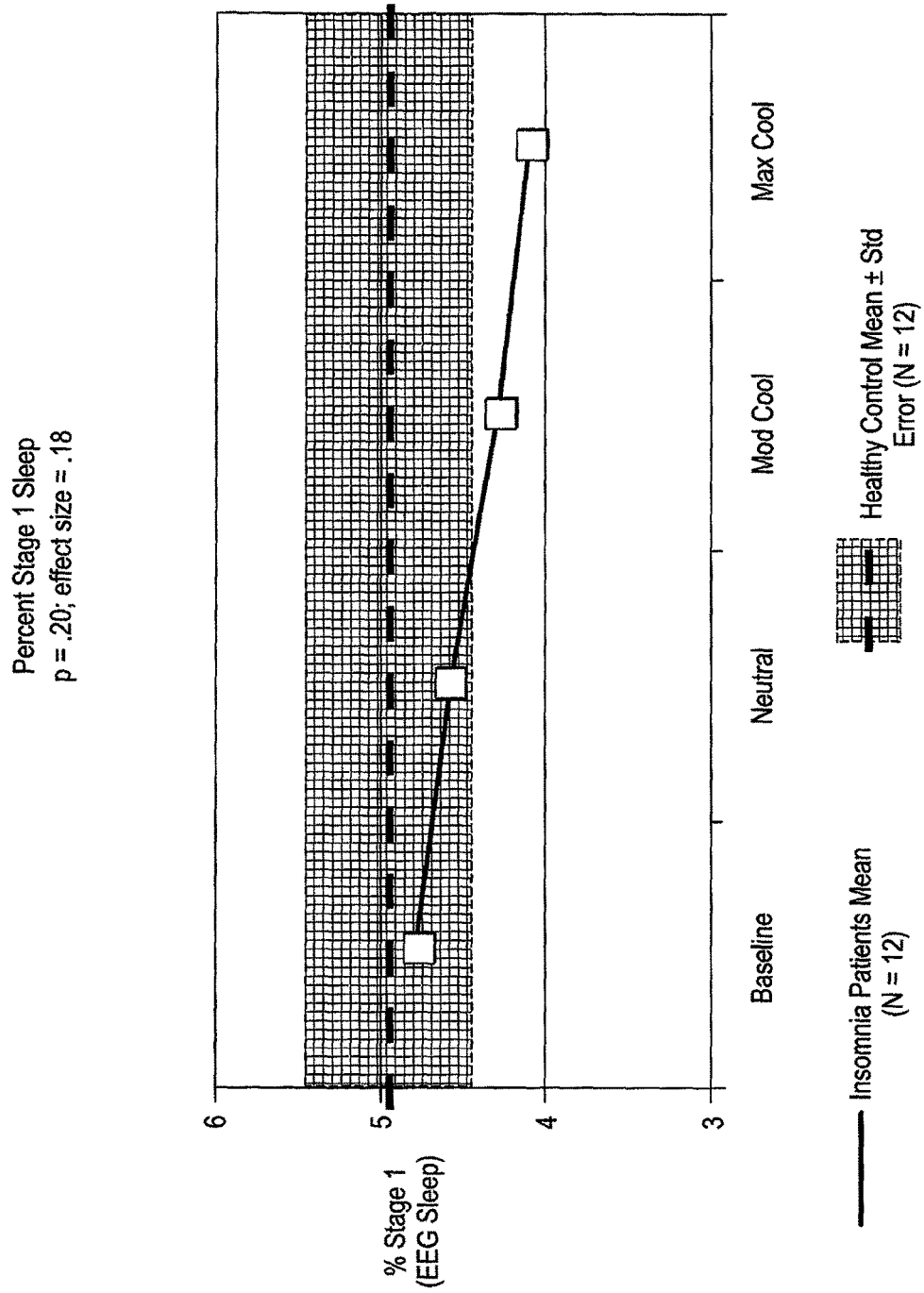
FIG. 5G shows the effect of one variation of a device for applying prefrontal hypothermia on the percentage of stage 1 sleep in an insomniac patient compared to non-insomniac.
Figure 5H:
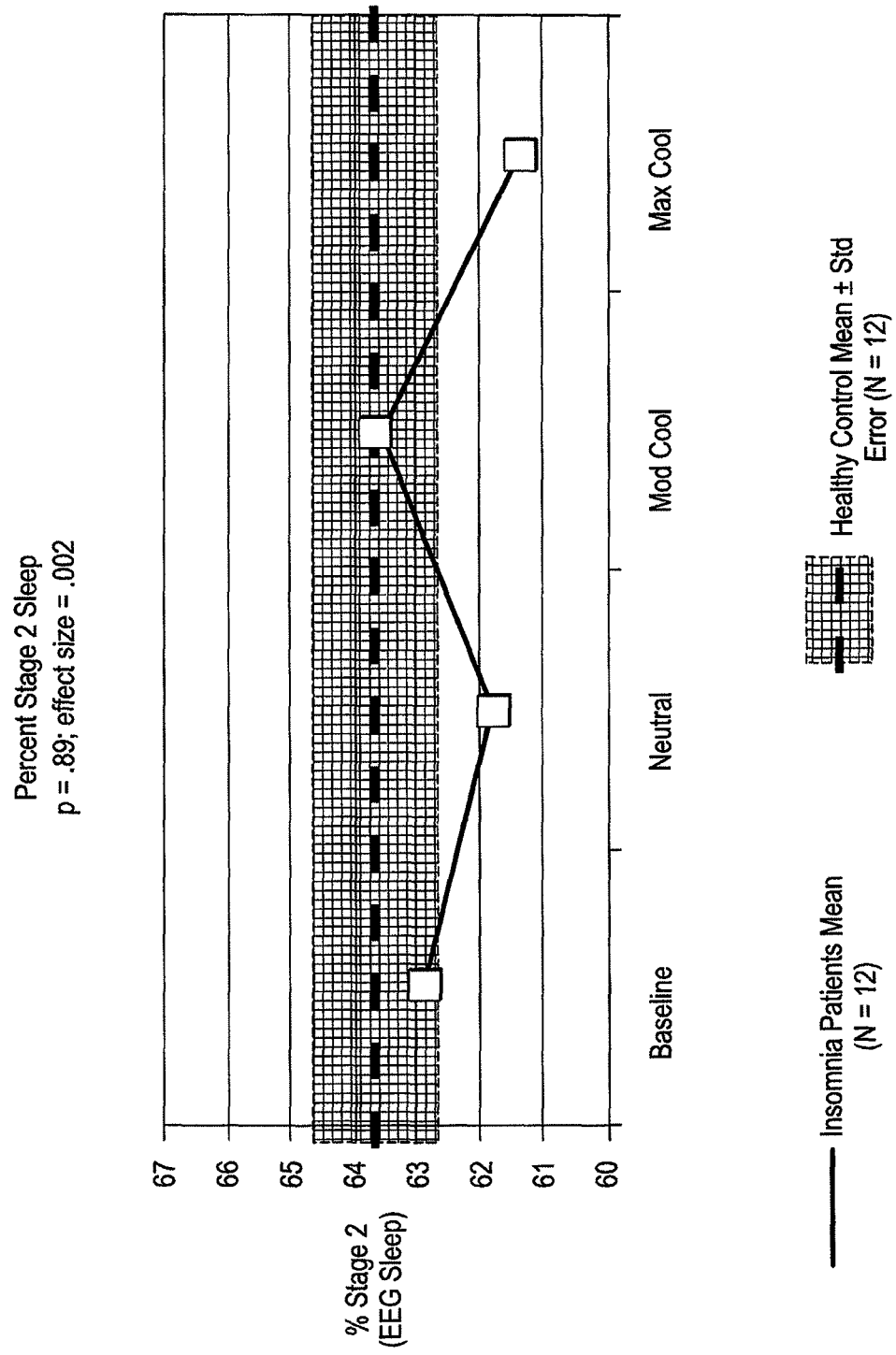
FIG. 5H shows the effect of one variation of a device for applying prefrontal hypothermia on the percentage of stage 2 sleep in an insomniac patient compared to non-insomniac.
Figure 5I:
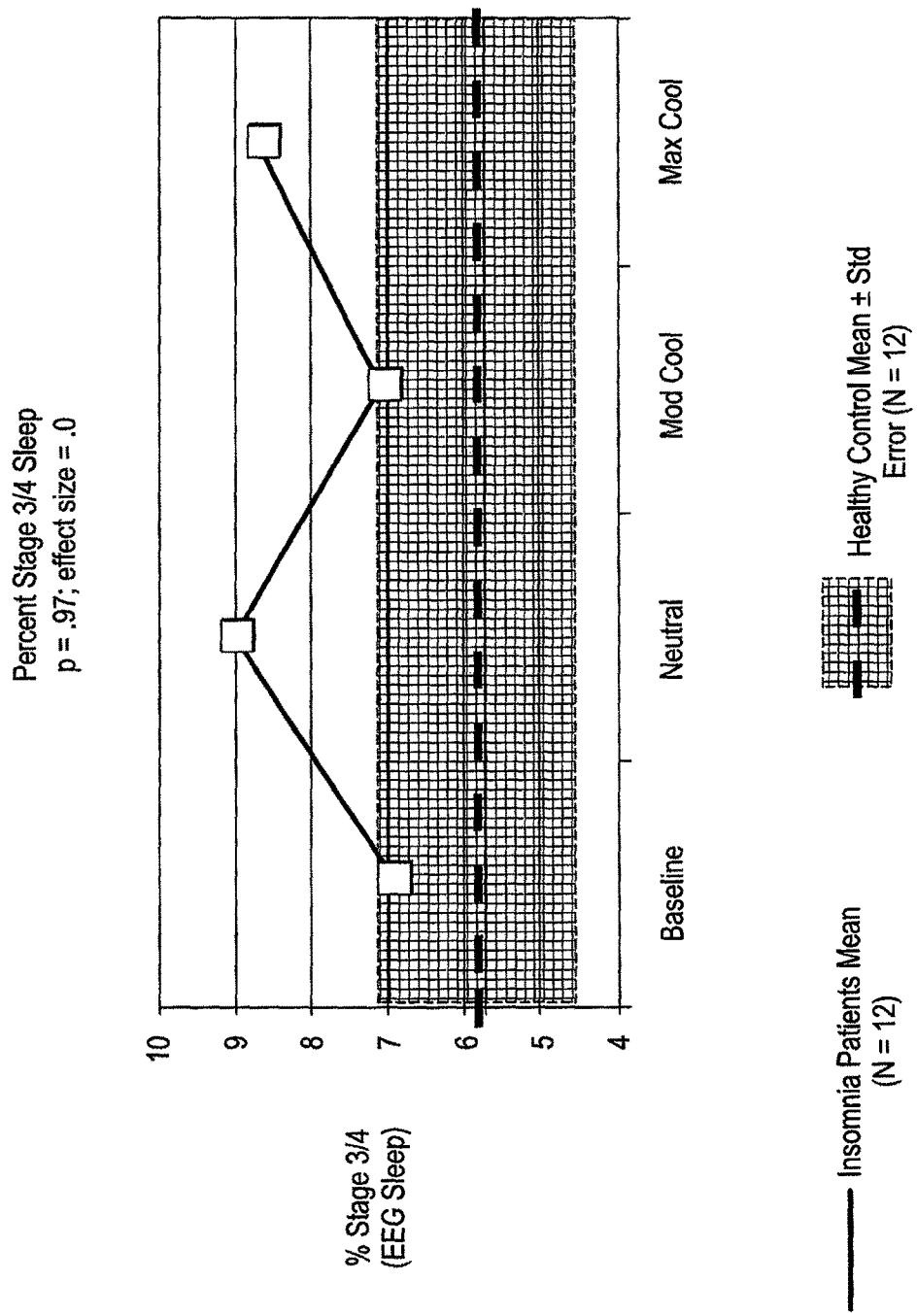
FIG. 5I shows the effect of one variation of a device for applying prefrontal hypothermia on the percentage of stages 3/4 sleep in an insomniac patient compared to non-insomniac.
Figure 5J:
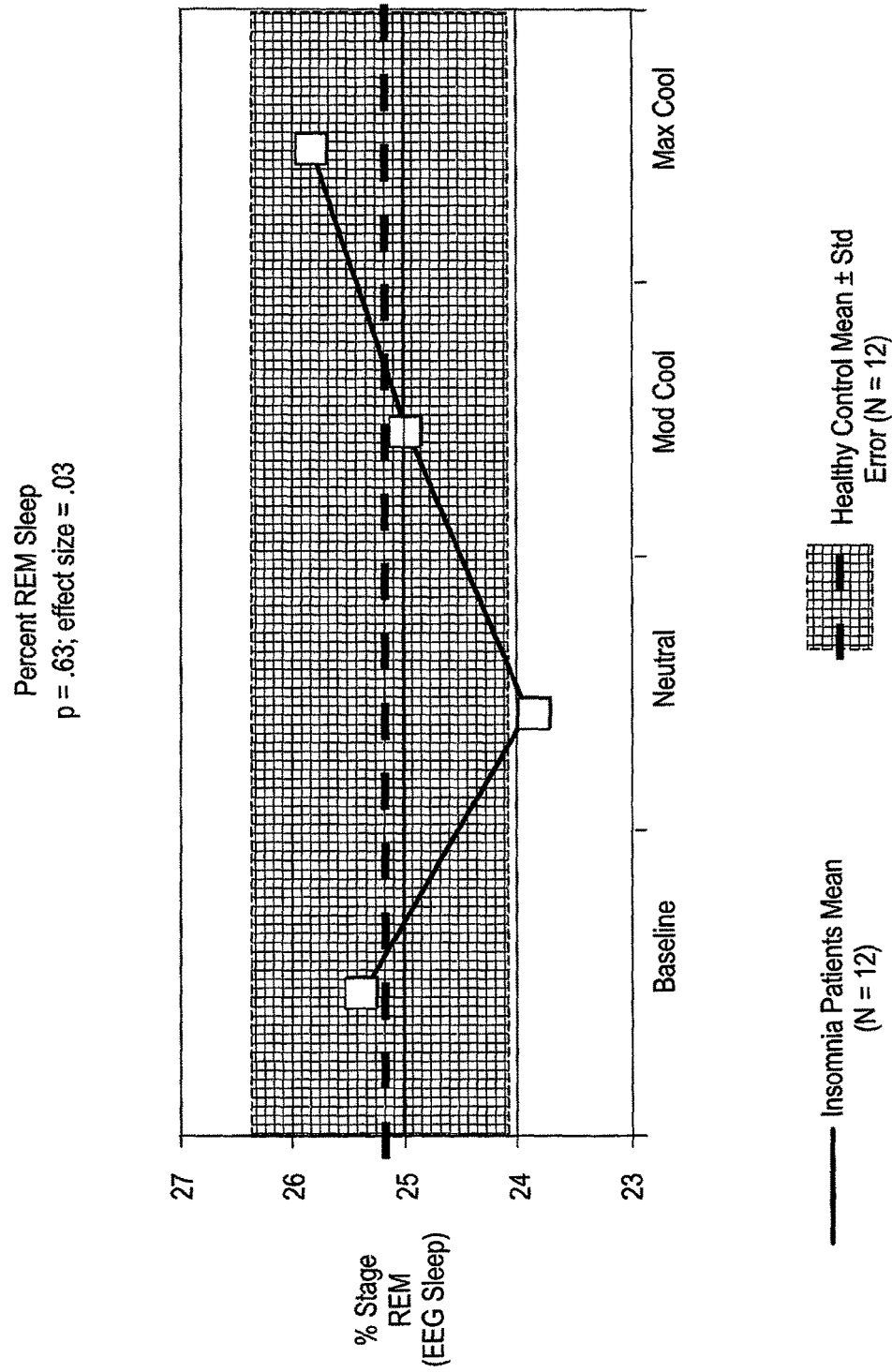
FIG. 5J shows the effect of one variation of a device for applying prefrontal hypothermia on the percentage of REM sleep in an insomniac patient compared to non-insomniac.
Figure 5K:
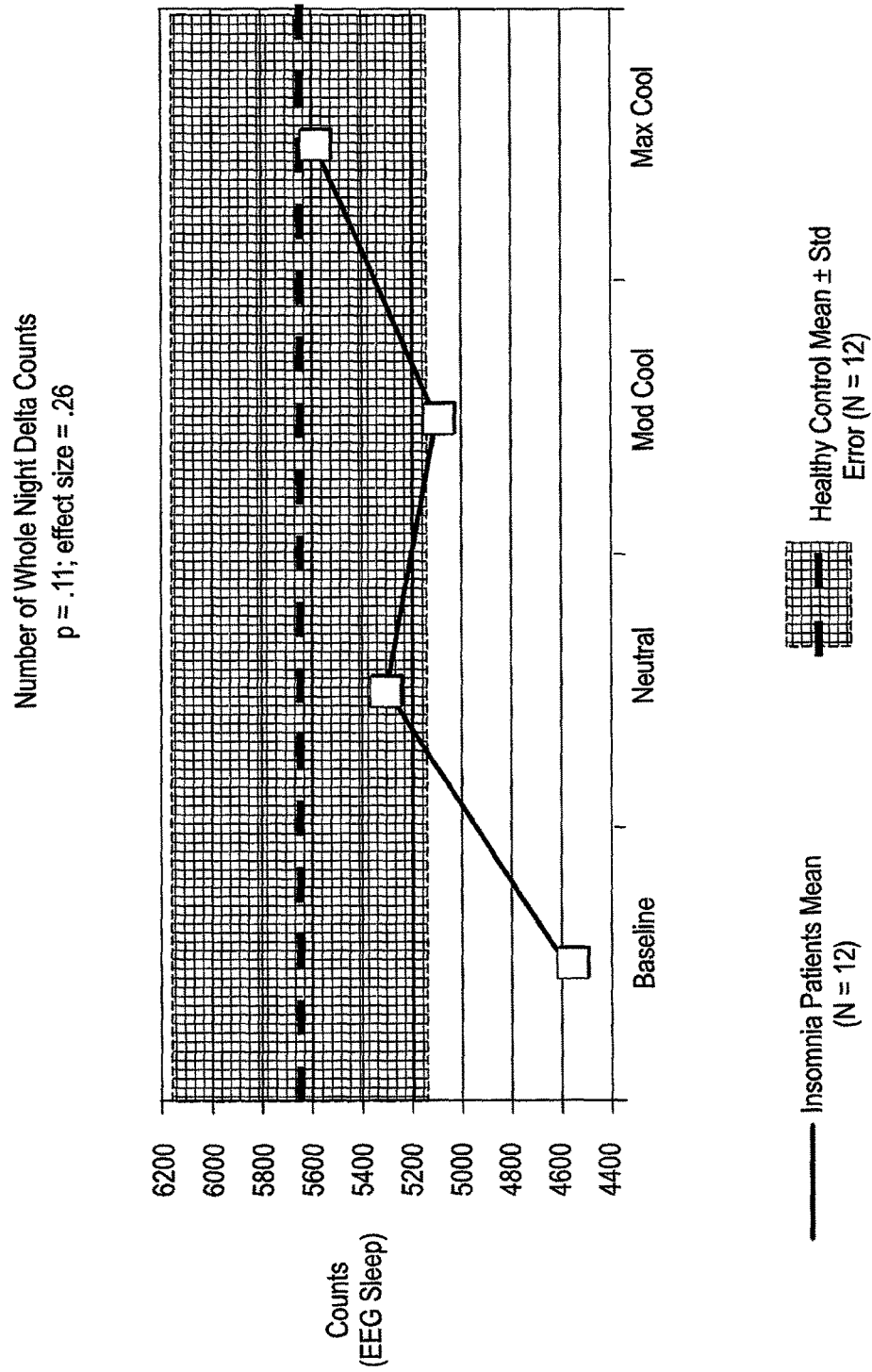
FIG. 5K shows the effect of one variation of a device for applying prefrontal hypothermia on the number of whole night delta counts in an insomniac patient compared to non-insomniac.
Figure 5L:
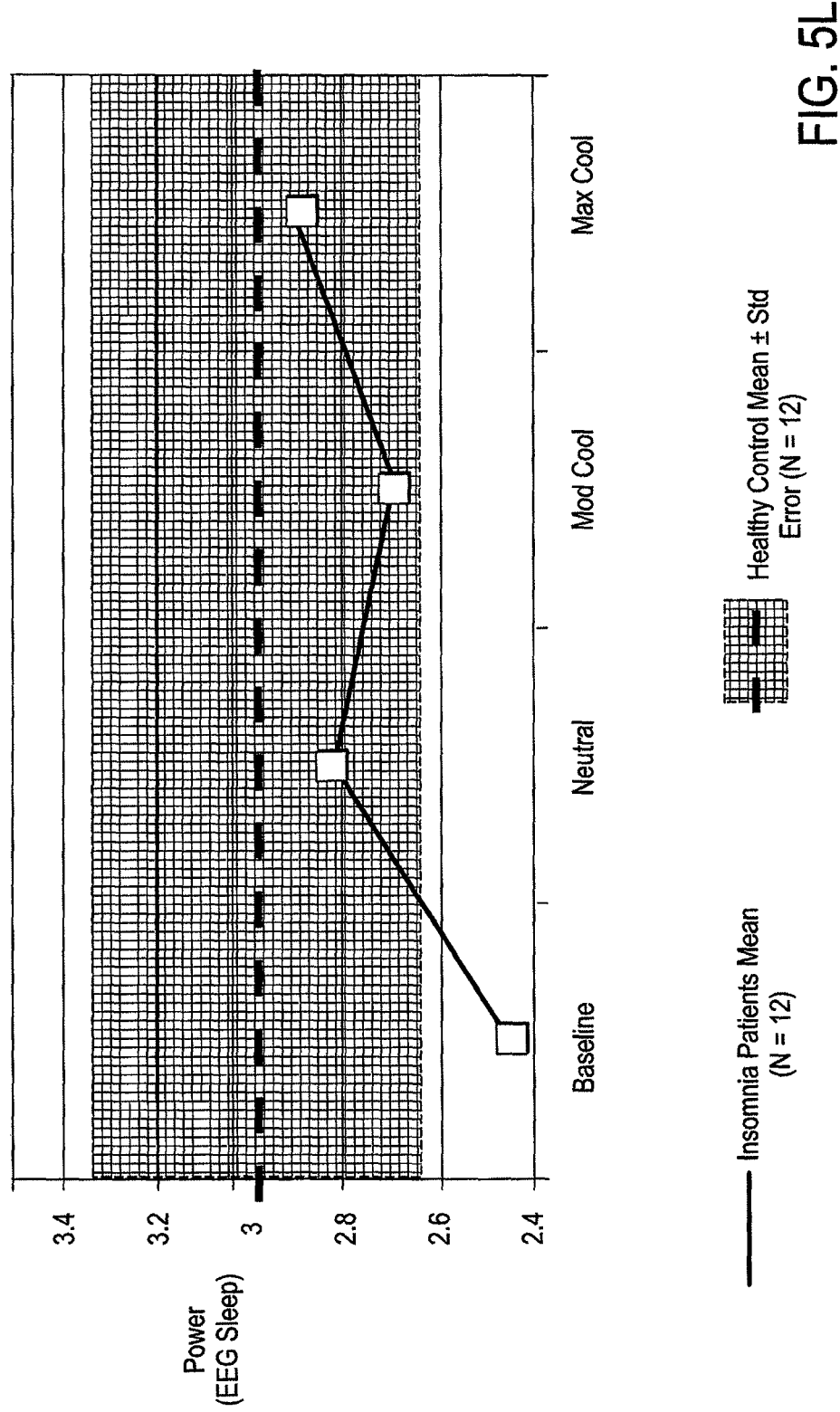
FIG. 5L shows the effect of one variation of a device for applying prefrontal hypothermia on the whole night spectral power in an insomniac patient compared to non-insomniac.

Hypothermic treatment increased the total sleep time (as shown in FIG. 5E) and increased the overall sleep efficiency to within "normal" ranges (FIG. 5F). In addition, hypothermic treatment also shifts EEG sleep stages to deeper stages of sleep, as illustrated in FIGS. 5G-5I. In addition, in these experiments hypothermic treatment also increases slow wave sleep toward healthy levels (FIGS. 5J-5L).

The above effects appear to be dose-dependent, particularly during the early period of application (e.g., sleep onset and early maintenance), with increasing levels of improvement from a neutral temperature to 22° Celsius to 14° Celsius. Thus, depending on the type of sleep desired, it may be possible to vary the temperature in a regulated manner across a night of sleep to alter sleep in a characteristic manner. Varying the temperature may also allow decreased power requirements for the system. Feedback relaying information regarding the type of sleep achieved may also be used to refine the temperature algorithm in a real time manner.

Devices and Systems

Various devices and systems for applying hypothermal treatment to the skin over the prefrontal cortex are described herein. In general these devices include at least one thermal transfer region (e.g., thermal transfer pad) which is configured to cool the skin above the prefrontal cortex.

The thermal transfer region may be any appropriate configuration, particularly those described below. For example, a thermal transfer pad may be shaped to cover the region of the forehead that overlies the frontal cortex of the brain. As described above, the frontal cortex is thought to be important for producing the restorative aspects of sleep based on sleep deprivation studies. Following sleep deprivation, the amount of slow wave sleep, a correlate of the homeostatic function of sleep, is increased in recovery sleep. The increase in slow waves is regionally maximal in the frontal cortex. The frontal cortex has also been shown to show greater reductions in metabolic activity during a recovery night of sleep following sleep deprivation than in relation to regular sleep. Cognitive deficits related to sleep deprivation have also been observed to be in realms thought to be related to frontal cortex function. Brain imaging and EEG sleep research studies described above show that application of a cooling stimulus over the forehead in a shape similar to that of the frontal cortex reduces metabolic activity in the underlying frontal cortex and this is associated with an increase in slow wave sleep, reductions in sleep latency, reductions in wakefulness after sleep onset, an increase in the duration of sleep at night in insomnia patients. Finally insomnia patients have been shown to have increased whole brain and increased frontal cortex metabolism during sleep that is related to their tendency to wake up across a night of sleep.

In some variations, the thermal transfer region may be part of a mask, garment, or other device that directs thermal transfer to the region of the scalp over the frontal cortex to benefit sleep. In some variations the thermal transfer region is limited to cover all or a portion of the frontal cortex. Thus, in some variations the system is configured to limit the region of thermal transfer to the skin region (e.g., forehead).

In some variations the shape of the thermal transfer region (e.g., pad) is custom-shaped to minimize overlap with the hairline of the individual wearing the pad, so as to minimize disruption of hair styles/patterns across a night of sleep. In this arrangement, the shape would maximize the available skin area that is not covered by hair for minimizing interactions with hair styles.

The thermal transfer region may be temperature-regulated by any appropriate mechanism, including air- or water-cooling, as well as solid-state cooling (e.g., Peltier devices), or some combination of these. In variations in which the thermal transfer region is liquid (e.g., water or other liquid coolant) cooled, the system may include a reservoir of cooling fluid that may be located separately from the rest of the device. For example, a mask or thermal applicator (including a thermal transfer region for contacting the patient's skin over the prefrontal cortex region) may be connected by tubing to the reservoir of cooled fluid. The cooled fluid may be pumped through the thermal transfer region to cool the skin and therefore apply hypothermic therapy to the prefrontal cortex. In general, any appropriate method of cooling the thermal transfer region may be used, including non-fluid or non-thermoelectric methods. For example, the thermal transfer region may be cooled by gas, or phase change of liquid/gas, or other chemical endothermic reaction.

In variations including tubing, the tubing may be positioned for optimal comfort during sleep. For example, in some variations, tubes that direct thermal transfer fluids to the mask may be configured to connect away from the patient so that they do not interfere with patient's sleep or risk entanglement with the patient's head or neck as the patient is sleeping with a device on their head. In some variations, the thermal transfer region is connected to the cooled fluid source by inlet/outlet tubing coming out middle of forehead region of the mark or applicator. Individuals tend to sleep on their sides or backs such that the sides of the head and the back of the head can come in contact with the sleeping surface or pillow.

Alternatively, in some variations any inlet/outlet tubing extends from the top of the mask, which may be useful when individuals sleep with their face down. The tubing may be made to swivel, bend, rotate, or flex relative to the mask. For example, a junction between the applicator and the tubing may be a rotating and/or swiveling junction, and may be flexible (particularly compared to more rigid applicator and tubing regions surrounding it).

The thermal transfer region may be connected and held to the patient's head in any appropriate manner. Similarly, any tubing extending from the applicator may be strapped or held so that it extends over top of head and exits middle of head. Another arrangement for connectors and tubing may be over the forehead and out the top of the head, since this part of the head generally does not come in contact with the sleeping surface or pillow. In an alternate configuration, the inlet/outlet tubing coming out over the sides over temples is shaped or configured to course around ears to back of head. Thus in one arrangement, tubing and connectors course over the temples and around the ears to the back of the head. In this arrangement, any tubing and connectors may be made relatively flat to minimize discomfort when the head is lying on them during sleep. The tubing may also be configured so as not to leak or collapse, limiting the heat transfer. Finally, the tubing may be insulated.

The systems described herein may be configured to be worn by the subject every night, and thus may include a washable, disposable, or replaceable skin-contacting region. In some variations the entire applicator is disposable; in other variations only a portion is disposable. For example, the thermal transfer region may be covered by a disposable material or cover that can be replaced nightly with each use. The disposable region (e.g., cover) is generally adapted to transfer heat over all or a portion, so that the thermal transfer region may effectively apply hypothermic therapy to the skin over the frontal cortex. In some variation this cover is configured as a disposable biogel cover.

In some variations the side tubing is integrated with one or more straps for holding the applicator that extend around the back of head. In any of these variations, straps may be utilized to keep the mask on the head and include tubing and connectors integrated into the strap in order to minimize excess tubing/connectors/materials coming off of the mask.

In some variations the system includes a chin strap to help with keeping cap from rising off top of head. In this arrangement, a piece of material comes off the sides of the mask and wraps under the chin of the wearer. The purpose of this is to keep the mask from sliding off the top of the head as may occur during position changes across a night of sleep. In some variations, strap tighteners on front of applicator may be used for easy adjustment and minimal interference with back of head lying on pillow. Any appropriate material may be used for fastening or fasteners, such as Velcro, adhesives, snaps and other types of fasteners, particularly those that minimize any bulk in areas of the mask or straps that might produce discomfort. An example would be having the fasteners in the forehead region where they would not interfere with mask comfort when the head is lying on the sleeping surface.

In some variations the system may include one or more molds for approximating forehead shape in general for similarly sized foreheads and specific forehead moldings for individuals for their unique head size. For example, the materials used for the mask may be specifically molded for the general shape of a head and even more specifically may be molded specifically for each individual who uses the mask to help with sleep. In general the thermal transfer region may have surface that is configured to maximize surface contact of the thermal transfer region to the head surface (skin) to increase the efficiency of heat transfer to the underlying cortex. This can be done by any permanent means such as producing a fixed size mold using a nonmalleable material, or may be done by any means in which some malleable material can be temporarily shaped to the surface features after it has been placed on the head. Examples might include some form of expandable material with a gas or fluid filled cavity that can be inflated, or expanded to conform to the shape of the underlying head, foams, shape-memory materials, or the like.

For example, in some variations the applicator includes one or more injection/vacuum chambers built into cap to increase comfort and increase surface contact for maximizing thermal transfer. Injection or vacuum chambers may be integrated into the mask and can be inflated or deflated to form the mask material to the shape of the head. After placing the mask on the head, either removing liquids or gases from chambers on the underside of the mask or injecting liquids or gases into some outer layer may conform the mask to come in closer approximation to the skin and given the natural curvature of the forehead may create an adhesive seal in which the mask may stay on the head. In one variations the applicator (e.g., mask) has a strapless design using only forehead shape and using injection/vacuum chambers and/or adhesive materials to maintain position of applicator. In this arrangement, some form of temporary adhesion produced by either an adhesive material or some combination of inflation/deflation, or temporary malleability of some material in the mask may serve the purpose of affixing the mask such that additional strappings or coverings to keep the mask in place are not necessary. This strapless arrangement of the applicator may offer increased comfort for some sleeping individuals so that no materials come between the sides and backs of their heads as they lay down for sleep.

In some variations, an integrated eye pad may be included to block out light and/or provide additional cooling of orbital frontal cortex to reduce metabolism in orbital frontal cortex before and during sleep.

In another arrangement, the mask may be constructed such that in addition to covering a region of the head over the frontal cortex, additional materials extend down to cover the orbits over the eyes. This material could serve several functions. First, it may have thermal transfer materials integrated into it so that the orbit is cooled with the intent of cooling the underlying orbitofrontal cortex which may facilitate the metabolic reduction in frontal cortex areas that are conducive for sleep. Another function of this material is to block visual sensory stimuli that could interfere with sleep given the known effects of light on brain arousal. Another function of this material may be to produce a relaxing, stress and anxiety reducing effect caused by the sensation of cooling thermal transfer in this head area. This in itself may facilitate sleep in addition to the effects on underlying brain metabolism. In some variations, the applicator may include thermal insulation around the thermal transfer region to prevent cooling of adjacent region (including the orbits of the eyes), which may be unnecessary and uncomfortable.

In some variations the device may include an integrated ear pad option to either block out noise and/or supply audio input during sleep. For example, the applicator may be configured such that in addition to covering a region of the head over the frontal cortex, additional materials extend down to cover the ears. This material could serve several functions. First, it may have thermal transfer materials integrated into it so that the ear cavities, canals and sinuses are cooled with the intent of cooling the underlying temporal cortex which may facilitate the metabolic reduction in temporal cortex areas that are conducive for sleep. Alternatively or additionally, this material may block auditory sensory stimuli that could interfere with sleep given the known effects of sound on brain arousal and/or may produce a relaxing, stress and anxiety reducing effect caused by the sensation of cooling thermal transfer in this head area. This may facilitate sleep in addition to the effects on underlying brain metabolism.

In some variations the applicator may include (or be configured for use with) an integrated neck pad to provide thermal stimuli to neck arteries to cool the brain before and during sleep to reduce cerebral metabolism before and during sleep and thereby improve sleep quality. Several arteries course through the neck in close approximation to the surface of the neck skin. In another arrangement, the mask would be constructed such that in addition to covering a region of the head over the frontal cortex, additional materials extend down to cover the neck. This material could serve several functions. First, it may have thermal transfer materials integrated into it so that the neck is cooled with the intent of cooling the underlying arteries that supply blood to the brain as a whole which may facilitate a reduction in whole brain metabolism that are conducive for sleep. Another function of this material may be to produce a relaxing, stress and anxiety reducing effect caused by the sensation of cooling thermal transfer in this head area.

In another arrangement, the mask may be constructed such that in addition to covering a region of the head over the frontal cortex, additional materials extend down to cover the sides and back of the neck. This additional material may have thermal transfer materials integrated into it so that the neck is cooled with the intent of cooling the underlying brain regions such as the brainstem, cerebellum and occipital cortex which may facilitate a reduction in metabolism to these regions of the brain that may be conducive for sleep. This material may also produce a relaxing, stress and anxiety reducing effect caused by the sensation of cooling thermal transfer in this head area. This in itself may facilitate sleep in addition to the effects on underlying brain metabolism.

In some variations the system may be configured to provide cooling stimuli to nasal cavities/oropharynx before and during sleep for purpose of cooling/reducing metabolic activity in brainstem/hypothalamus to facilitate sleep. For example, in another arrangement, methods to provide thermal transfer in the area of the nasal cavities/oropharynx in the back of the throat and nasal passages may be applied to cool the underlying brain regions such as the upper brainstem, hypothalamus and orbitofrontal cortex which may facilitate a reduction in metabolism to these regions of the brain that may be conducive for sleep.

In general, the devices and systems may be used combination with (and may be integrated as part of) any other device intended to be worn by a patient during sleeping. For example, devices to treat respiration (e.g., respirators, ventilators, CPAP machines, etc.) may include integrated cooling systems such as those described herein to help enhance sleep, and/or treat sleeping disorders.

As mentioned above, the system described herein may generally include one or more sensors for monitoring either or both the patient and the system components (e.g., thermal transfer region). In some variations the system is configured to measure various parameters on the applicator, including temperature sensors (to measure skin temperature) or electrodes (e.g., to measure EEG parameters) or the like. The system may be configured to provide feedback to the patient/clinician and/or to provide feedback to the system (e.g., the controller) to modify activity of the system.

In addition, in some variations the systems and devices described herein may include additional therapeutic or non-therapeutic modalities which may enhance comfort, relaxation and/or sleep. For example, the systems described herein may include one or more vibratory actions or mechanisms to induce a vibratory/rhythmic/movement sensation on the skin. In one arrangement of the device, a physical sensation may be created that could facilitate sleep and/or produce a relaxing, anxiety or stress reduction purpose that could facilitate sleep and add to the other effects of the device as otherwise noted. For example, physical turbulence in the fluid channels may be permitted or generated. In this arrangement of the device, the direction and movement of fluid within the channels of the thermal transfer pad are configured to have a pleasing, relaxing, calming, stress reducing, massage like effect that could potentiate the positive sensations of the device for the wearer. Similarly, altering pumping pressures of the fluid in a rhythmic manner may be optimized for comfort, soothingness, massaging feeling. In this arrangement of the device, the direction and movement of fluid within the channels of the thermal transfer pad could be altered by various configurations of alternating pressure cycles in the pump, thereby creating a more pleasing, relaxing, calming, stress reducing, massage like effect that could potentiate the positive sensations of the device for the wearer.

In some variations, the system may incorporate a smell or odor stimuli to help enhance comfort and/or effect. For example, the addition of aromas may be subjectively consistent with relaxation/sleep. In this arrangement of the device, the smell of the thermal transfer pad could be altered by various scents, thereby creating a more pleasing, relaxing, calming, stress reducing, effect that could potentiate the positive sensations of the device for the wearer.

As mentioned above, the system may include either direct or indirect modulation of sound when using the device. In general, sounds subjectively consistent with relaxation/sleep may be emitted by the systems (either as part of the applicator or as part of the nearby device, even in variations not including earphones/headphones or the like. In this arrangement of the device, sounds could be added to the thermal transfer pad or (for devices having a remote source of cooling fluid) to a remote unit connecting to the thermal transfer pad, thereby creating a more pleasing, relaxing, calming, stress reducing, effect that could potentiate the positive sensations of the device for the wearer. As mentioned above, the device may include integrated ear pads or plugs with the thermal transfer pad to block out unwanted environmental noises that might interfere with sleep. In another variation of the device the system may be configured to emit white noise, or blocking noises, thereby cancelling out intermittent, variable noises in the environment of the sleeping individual.

Controller

Any of the systems described herein may include a controller for regulating the temperature of the thermal transfer region and thereby providing hypothermic therapy. In general, the controller (which may be referred to as a hypothermic controller) may control both the applied temperature and the timing (or time-course) of the applied temperature. The controller may be typically configured to apply one or more temperatures to the thermal transfer region for a predetermined amount of time, including following on or more time course for application of cooling. The controller may include a plurality of inputs, including user-selectable inputs (controls for timing, on/off, etc.), as well as feedback (e.g., from the skin surface, or other system feedbacks as described below).

A dose or time course for activation may be referred to as a timeline, or algorithms, of thermal transfer on sleep. For example, in some variations the system in configured to deliver a fixed time course. In one arrangement, a constant thermal transfer rate can be maintained without variation across the period of use. For example, the system may be configured to deliver a dose prior to sleep only. In one arrangement, the thermal transfer applicator could apply treatment for 45 minutes to 1 hour prior to getting in to bed to facilitate the sleep onset process. For example, the system may be configured to cool the thermal transfer region to approximately 14° C. to facilitating sleep onset; based on patient comfort, this temperature may be adjusted to higher temperatures (e.g., up to 30° C.), or it may be a fixed temperature. Similarly, the system may be configured to ramp down to the final temperature (e.g., of 10° C., 14° C., etc.) to allow a subject to acclimate to the temperature). In this application, if effects on only sleep onset were desired, the device could be removed at the time a person got into bed.

In some variations, the system may be configured or adapted for use only when the patient has gone to bed, to operate even after the patient is sleeping. In one arrangement, the applicator could be worn or applied when a person got into bed, and hypothermic therapy applied over a portion or throughout a night of sleep to facilitate the sleep process (including across a night of sleep). In this arrangement, 14° C. or other low temperature (e.g., 10° C.) may be maximally effective, and higher temperatures less effective, in facilitating deeper sleep especially in the first half of the night, with less significant effects later in the night.

In some variations the system may be configured to provide hypothermal therapy both before desired sleep time (GNT) and after initially falling asleep. For example, in one arrangement, the thermal transfer pad could be applied 45 minutes to 1 hour prior to getting in to bed to facilitate the sleep onset process and left on throughout a night of sleep to facilitate the sleep process across a night of sleep. Thus, the controller may be configured to initially apply a sleep onset time course (e.g., ramping to a sleep-onset temperature such as about 14° C., and maintaining that temperature for a predetermined time period, such as 30 min-1 hr), and then transition to a sleep maintenance time course (e.g., maintaining the temperature at a relatively low temperature such as about 14° C. for the first 2-4 hours of sleep or for the rest of the night, or gradually increasing the temperature to a higher level thereafter). The maintenance time course may maintain deeper sleep across the night with lesser degrees of facilitation in higher temperatures up to 30° C.

Thus, in some variations the time course is constant, while in other variations, the time course is variable (including changes in the temperature over the sleep period). For example, in one arrangement, a variable thermal transfer rate with defined changes can be delivered across the period of use. While changes in device temperature are felt immediately at the skin surface, there is a delay between the time a cooling stimulus is applied to the head surface and the time cooling is achieved in the underlying cortex. Variable time course algorithms, therefore, may include different delays built in between the time of application and the time of the desired effect on either the temperature sensation at the skin surface or on the temperature of the underlying brain and resulting effects on brain metabolism. In one arrangement a delay of approximately 30 minutes may be built in to the systems variable time course algorithms.

In some variations the systems described herein are configured for use prior to falling asleep (which may be referred to as pre-cooling devices or systems). Thus, the device and method of operation may be configured specifically for being worn to increase drowsiness or decrease the latency to sleep of a patient. The device may be adapted by including timing controls adapted for the pre-sleep cooling described herein. In some variations the system may be configured to differentiate between long and short sleep periods; for example, the system may be configured to facilitate "napping" (short sleeps) or longer-duration sleeping. In some variations the system includes controls (and timers) for selecting sleep duration, and may alter the applied hypothermic therapy on the basis of the control. In the napping mode the system may provide an initially high level of cooling (e.g., to between 10° C. and 18° C.) and shift after a first time period to a higher temperature (e.g., 24° C., or some temperature between about 20-28° C.) or shift to a thermally "neutral" temperature (e.g., about 30° C.). In some variations, the system or device is configured as a "napping" device as opposed to a 6-8 hour sleep period device.

As mentioned above, in some variations the system includes one or more ramping time courses. For example, the thermal transfer region could be applied at a neutral temperature of approximately 30° C. at 45 minutes to 1 hour prior to getting in to bed, and then the temperature ramped down to approximately 14° C. (e.g., between 10 and 25° C.) over a matter of minutes, while adjusting the rate of ramping to skin surface comfort levels, to facilitate the sleep onset process. Similarly, any set temperature could be achieved by first applying the device at a neutral comfortable skin temperature then ramping the temperature over time to achieve the desired final endpoint temperature.

In some variations the time course may be varied based on either predetermined values or based on feedback. For example, a sleep maintenance time course may be applied that may include varying the time course of thermal transfer in coordination with the probability of NREM and REM sleep stage occurrences. Brain temperature as well as brain blood flow and brain metabolism vary in characteristic ways across a night of sleep and is dependent on the stage of sleep an individual may be in as well as the duration of time from the beginning of sleep. NREM sleep stages include lighter stage 1 sleep, deeper stage 2 sleep and deepest stages slow wave sleep with slow wave sleep predominating in the first half of the night. REM sleep occurs cyclically across a night, every 60-90 minutes with progressively longer and more intense REM periods occurring in the latter parts of the night. Brain temperature, blood flow and metabolism tend to lessen in deeper NREM sleep and increases in REM sleep. The degree to which these changes occur are thought to be functionally important for sleep. The cooling device may therefore facilitate the deepening of NREM sleep by applying a time course that mimics or follows the time course of a normal sleep cycle. This may result in reducing metabolic activity in the frontal cortex with consequent increases in slow wave sleep.

In one arrangement of a variable thermal transfer time course, therefore, the maximal cooling may be concentrated earlier in the night when slow wave sleep tends to be maximal, with less significant cooling towards the end of the night when REM sleep and natural brain warming would be occurring. One algorithm (e.g., time course) may therefore include a thermal transfer at the coolest temperature tolerated without discomfort (e.g., between about 10° C. and about 14° C. at the beginning of the night and ramping to a neutral 30° C. temperature by the end of a night's sleep). This ramping could be linear across the night, or could have a curvilinear component where maximal cooling is concentrated in periods where slow wave sleep has a high probability of occurring as revealed by normative curves of slow wave sleep production across the night.

It is known that some disorders, such as depression for example, have characteristic alterations in REM sleep. The dose-ranging research study above demonstrates that altering the temperature of the thermal transfer mask has predictable effects on the occurrence of REM sleep. One algorithm, therefore, may include a variable thermal transfer across the night that is intended to target the occurrence of REM sleep in a therapeutic manner. In depression, for example, where REM sleep duration and intensity seem to be more highly concentrated in the first third of the night, use of a time course having a temperature of the coolest tolerable temperature (e.g., 14° C.) over this period would be expected to inhibit abnormal REM sleep production whereas the use of more neutral temperatures in the latter half of the night would be expected to lead to more normal REM sleep production in that part of the night.

Similarly, alterations in REM and NREM sleep can occur in a variety of neuropsychiatric disorders. The general principle of altering the temperature of the thermal transfer region of the applicator to facilitate or diminish discrete aspects of deep NREM sleep or REM sleep that are directly related to the specific disorder would be expected to have therapeutic utility specific to the disorder.

As mentioned briefly above, the system may include feedback to the controller to regulate the applied hypothermic therapy. Surprisingly, altering the applied hypothermic therapy has a predictable effect on sleep physiology, as described above. It may be possible, therefore, to measure the changes in sleep physiology and incorporate them into a feedback loop that then results in changes in the thermal transfer. In this manner, the amount of thermal transfer applied can be adjusted in real time to achieve some desired physiological effect.

In one arrangement a variable thermal transfer rate with defined changes can be delivered across the period of use with the changes linked to feedback from changes in the physiology of the body across a period of use. Physiological measures may be monitored and thermal transfer adjusted in real time according to the level of the physiological measure. For example, the system may include feedback based on the presence or absence of REM or NREM sleep as assessed by any method of REM/NREM sleep assessment, such as EEG frequency, Heart Rate Variability, Muscle Tone or other mechanism. Thus, the device or system may include one or more sensors (electrodes, etc.) that provide at least some indication of sleep cycle, this information may be fed or monitored by the controller, which may modulate the applied dose based on the detected REM/NREM status. The perceived status may be compared to an expected or desired status, which may alter the applied hypothermic therapy.

In some variations, the system may also or alternatively monitor and/or react to the depth of slow wave sleep, as measured by EEG wave analysis or other mechanism. Similarly, the system may monitor and/or respond to the degree of autonomic arousal as measured by HR variability or other mechanism. Other examples of characteristic that may be (separately or in combination) monitored and/or feed back into the system to modulate the applied hypothermy is galvanic skin response, skin temperature, eye motion during sleeping, and gross body motion during sleeping. For example, skin temperature may be measured either at the skin on the head underneath the device, or on skin at some other portion of the head not underneath the device, or peripheral skin temperature, or core body temperature (measured internally or by some external means) or some combined measure assessing thermoregulation of the head and periphery, or core body to peripheral temperature measure. Eye motion or body motion may be monitored optically or through one or more motion or position sensors (including acceleratomers).

In many of the systems and devices described herein the control may be adjusted by the subject wearing the device (and/or by a physician or other professional). In some variations, the person wearing the device can modify the thermal transfer rate across the period of use with the changes linked to subjective feedback. For example, a control on the device may allow the person wearing the device to adjust the temperature according to their immediate comfort and treatment needs, either up or down some small increments.

In another arrangement, an individual can set their go to bed times and desired get out of bed times, then a preprogrammed algorithm is input to start and stop at those times and provide the incremental adjustments to occur on a relative basis over this time period. These automated time calculations could be implemented for any variable schedule of thermal transfer rates across any defined period of time.

In general, the temperature of the skin beneath the applicator (e.g., the thermal transfer region of the applicator) may also be monitored. Although the system and/or device may apply a predetermined temperature to the skin through the applicator, the temperature of the skin does not necessarily become cooled to this temperature, but is typically higher. In some variations skin temperature beneath the thermal transfer region may be monitored and/or fed back into the controller to regulate the applied temperature. As mentioned above, the thermal contact between the skin and the applicator may be optimized or regulated. For example, the materials forming the applicator (and particularly the thermal transfer region) may be optimized or otherwise selected to determine the temperature applied. In one variation the lining of the transfer pad that comes in contact with the skin is a hydrogel allowing for increased surface area contact and increased thermal transfer characteristics. In another arrangement, this lining is combined with dermatologic products that can be rejuvenating for the skin when in contact over the course of a night. In another arrangement, an inner lining can be refreshed on a nightly or less frequent basis that can benefit the skin when applied over the night of sleep.

During the daytime, when not in use, the cooling chamber, any tubing and headgear may be stored until the next night's use. In some variations the device is self-contained (e.g., battery powered, particularly for solid-state devices). Thus the device may be re-charged when not in use. In one arrangement, the equipment can all be contained in a storage box for an attractive appearance, which may also be functional (e.g., recharging, sanitizing, protection, etc.). In variations including tubing, the tubing can automatically recoil into a storage region (e.g., box) when not in use for maintaining an attractive appearance. In some variations, the applicator is stored with antiseptic materials and/or in an environment that provide for antiseptic cleaning and storage to minimize the potential for growth of organisms that may be harmful to the wearer.

Because the device is intended for use at night, the controls may be optimized for use in low lighting. A subject using the device may have to interact with the device at night when illumination would be expected to be low, thus in some variations, the device or system includes control features that the individual needs to interact with would become lit only when an individual comes in close contact with the device.

In another arrangement of the device, control features may be made of an illumination level that minimally interferes with sleep. In another arrangement of the device, control features may be voice activated. In another arrangement of the device, control features have physical features that can be identified by touch and differentiate themselves from other parts of the device to let an individual know in the dark where the control buttons are located.

In general, it may be particularly desirable to include one or more features that record (and/or analyze) use of the device or system. For example, in the clinical management of a patient, a healthcare provider may want to know certain parameters of the patient and/or device over multiple nights of use such that care can be optimized. In some variations, the system or device includes memory (e.g., a memory card or memory chip) that may automatically record certain parameters and store them for later display by the healthcare provider. For example, the operation of the controller may be recorded.

In monitoring their own care, a device user may want to know certain parameters of the patient and/or device over multiple nights of use such that care can be optimized. In one arrangement of the device, therefore, memory may automatically record certain parameters and store them for later display. This information could be transferred to a healthcare provider's office or some other central database via the phone or interne or some wireless technology where someone could review the information and provide recommended adjustments in the treatment accordingly. Examples of information that may be stored could include, but would not be limited to: temperature of the device; skin temperature; core body temperature; measures of autonomic variability; depth of sleep as assessed by NREM sleep, EEG power in discrete frequency bands, REM sleep or other sleep staging; periods of activity and/or wakefulness across the night; subjective measures of sleep depth/comfort/satisfaction; and sleep duration.

In some variations this information may be automatically collected, while in other variations it may be entered by the subject or a third party.

Indications and Methods for Operation

As mentioned above, the systems and devices described herein may generally be used to treat sleeping disorders. In particular, these systems and methods may be used to treat insomnia. Thus, the systems and devices described herein may be used to facilitate sleep. For example, the systems and devices described herein may be used to decrease sleep latency (e.g., the time to fall asleep), and/or increase sleep duration.

In operation, a method of modulating sleep (e.g., increasing sleep duration) may include the steps of positioning and/or securing the thermal transfer region on the forehead or scalp of the subject (who may also be referred to as a patient) in the region over the area of the frontal cortex and (in some variations) related areas. The system or device may then apply hypothermic therapy (e.g., cooling) to the skin to reduce metabolic activity in the underlying frontal cortex and related areas thereby facilitating or modulating sleep.

As discussed above, in some variations the systems and device may be applied prior to sleep to aid in sleep onset. For example, the system may include the step of applying the thermal transfer region in contact with the skin over the prefrontal region for a time period (e.g., 15 minutes, 30 minutes, 45 minutes, 60 minutes, etc.) before a desired good night time (GNT, the desired time to fall asleep). Regional hypothermia may be used alone or in conjunction with other relaxation and/or pre-sleep therapies to enhance sleepiness and decrease the latency to sleep.

In some variations, the method of use may include (or be limited to) a method of increasing slow wave sleep, a method of increasing sleep maintenance, a method of reducing awakenings, and/or a method of increasing the time spent asleep across the night. In general, each of these methods may include the steps of placing the applicator (including the thermal transfer region) in contact to transfer thermal energy from the subject's skin above the prefrontal cortex. Thereafter, the system may execute a treatment regime including cooling to a temperature such as the lowest temperature that may be tolerated by the subject without resulting in discomfort (including arousals) such as pain or tissue damage. Typically this temperature may be between about 10° C. and about 25° C. (e.g., 11° C., 12° C., 13° C., 14° C., 15° C., 16° C., etc.). The temperature may be lowered slowly (e.g., in a ramp, such a linear ramp) or more quickly. The treatment regime may hold this first target temperature for a first time period (which in some cases may be a predetermined time period such as 1 hour, 2 hours, 3 hours, 4 hours, 5 hours, etc.) or it may be determined based on patient feedback and/or control setting. Thereafter the temperature may be increased and/or decreased in one or a series of dosage settings. In some variations the dosage follows a predetermined treatment parameter that increases the temperature from an initially low value to a slightly higher temperature later in the evening to help maintain sleep.

Any of the methods described herein may be used to treat insomniacs, however these methods may also be used to generally improve healthy sleep, even in non-insomniac subjects. In particular, these methods, devices and systems may be used to improve sleep in individuals who experience sleeplessness.

Further, the systems and devices described herein may be used as part of a method to treat and improve sleep in individuals with neuropsychiatric disorders such as, but not limited to, depression, mood disorders, anxiety disorders, substance abuse, post-traumatic stress disorder, psychotic disorders, manic-depressive illness and personality disorders and any neuropsychiatric patient who experiences sleeplessness.

Sleep reduction and disruption is known to be associated as a co-morbidity in a number of disorders, and the devices and systems described herein may be used to help alleviate such disorders, in part by helping modulate and enhance sleep. For example, the devices and systems described herein may be used to improve sleep in patients with pain, including chronic pain, and headaches, including migraine headaches, and cardiac, endocrinologic, and pulmonary disorders, and tinnitus.

The systems and devices may also be used in a waking subject to enhance relaxation and improve waking function. The treatment regime may be similar or different from the treatment regimes used to enhance sleepiness and/or prolong sleep. For example, the devices and systems described herein may be used to improve waking function by reducing metabolic activity in the frontal cortex during waking, including: reducing the experience and distress of tinnitus and chronic pain; increasing mental and cognitive focus; producing a subjective feeling of relaxation; producing a subjective feeling of soothing; producing a subjective feeling of comfort; producing a subjective feeling of stress reduction; improving mood in patients with depression; reducing fears, anxieties in patients with anxiety disorders; reducing distracting thoughts; and/or reducing obsessive thoughts, and behaviors.

In such non-sleeping variations, it may be useful to allow subject-control of the system, including subject control of the duration and level of cooling applied. In some variations pre-determined settings for different applications may be included as part of the system.

Another application of the systems and devices described herein includes thermoregulation and fever reduction. The devices and systems may be used to reduce generalized fever and could be utilized for fever control, particularly in individuals with elevated core body temperatures from a variety of causes, including, but not limited to, infection. In some variations the systems and devices described herein may be used or configured for use in conjunction with (or integrated into) a system for light therapy for Circadian Rhythm Disorders ("CRD").

In addition, the devices and systems described herein may also be used to alter circadian rhythms and could therefore be applicable for use in circadian rhythm disorders such as shift work disorder, phase advance and phase delay circadian rhythm disorders.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of enhancing sleep by non-invasively applying hypothermal therapy to at least a portion of a subject's frontal cortex, prefrontal cortex or frontal and prefrontal cortex, the method comprising:
    positioning an applicator comprising a thermal transfer region in communication with the subject's skin over at least a portion of the subject's frontal cortex, prefrontal cortex or frontal and prefrontal cortex;
    maintaining the applicator temperature so that the thermal transfer region is cooled to between about 10° C. and about 25° C.;
    maintaining the temperature for a time period extending at least 15 minutes.

2. The method of claim 1, further comprising maintaining contact between the subject's skin over the subject's frontal cortex, prefrontal cortex or frontal and prefrontal cortex and the thermal transfer region so that the metabolism in the cortex is slowed.

3. The method of claim 1, wherein positioning the applicator comprises securing the applicator in position.

4. The method of claim 1, wherein positioning the applicator comprises adhesively securing the applicator.

5. The method of claim 1, wherein positioning the applicator comprises securing the applicator over just the subject's forehead region.

6. The method of claim 1, further comprising ramping the temperature of the thermal transfer region from ambient temperature to the temperature between about 10° C. and about 25° C. over at least five minutes.

7. The method of claim 1, further comprising warming the thermal transfer region to a neutral temperature at the end of a night's sleep.

8. The method of claim 1, wherein maintaining the temperature comprises maintaining the temperature for at least 30 minutes.

9. The method of claim 1, wherein maintaining the temperature comprises maintaining the temperature for at least one hour.

10. The method of claim 1, further comprising changing the temperature of the thermal transfer region to a second temperature.

11. The method of claim 1, further comprising cooling the thermal transfer region to a second temperature that is between about 10° C. and 30° C.

12. The method of claim 11, wherein the second temperature is between about 20° C. and about 25° C.

13. The method of claim 11, further comprising maintaining the second temperature for a second time.

14. The method of claim 11, further comprising maintaining the second temperature for more than one hour.

15. The method of claim 11, further comprising maintaining the second temperature for more than four hours.

16. The method of claim 11, further wherein the second temperature is maintained by adjusting the temperature of the thermal transfer region based on feedback from the patient.

17. The method of claim 11, further wherein the second temperature is maintained by adjusting the temperature of the thermal transfer region based on subject selection of a user-selectable input.

18. The method of claim 1, wherein the method of enhancing sleep is a method of reducing sleep onset in a subject with insomnia.

19. A method of enhancing sleep by non-invasively applying hypothermal therapy to at least a portion of a subject's frontal cortex prefrontal cortex or frontal and prefrontal cortex, the method comprising:
    positioning an applicator comprising a thermal transfer region in communication with the subject's skin over at least a portion of the subject's frontal cortex, prefrontal cortex or frontal and prefrontal cortex;
    cooling the thermal transfer region to between about 10° C. and about 25° C.; and
    maintaining contact between the subject's skin over the at least a portion of the subject's frontal cortex, prefrontal cortex or frontal and prefrontal cortex and the thermal transfer region for at least 15 minutes.

20. The method of claim 19, wherein maintaining contact comprises maintaining the contact between the subject's skin over at least a portion of the subject's frontal cortex, prefrontal cortex or frontal and prefrontal cortex and the thermal transfer region for at least 30 minutes.

21. The method of claim 19, further comprising warming the thermal transfer region to a neutral temperature.

22. The method of claim 19, further comprising cooling the thermal transfer region to a second temperature between about 10° C. and 25° C.

23. The method of claim 19, further comprising maintaining the temperature of the thermal transfer region between about 10° C. and about 25° C.

24. A method of enhancing sleep in a subject by non-invasively applying hypothermal therapy to at least a region of the subject's frontal cortex, prefrontal cortex or frontal and prefrontal cortex, the method comprising:

positioning an applicator comprising a thermal transfer region in communication with the subject's skin over at least a portion of the subject's frontal cortex, prefrontal cortex or frontal and prefrontal cortex; and maintaining, after the subject has fallen asleep, the thermal transfer region between about 10° C. and 25° C. for a first time period extending at least 30 minutes.

25. The method of claim 24, wherein maintain comprises maintaining the thermal transfer region between about 10° C. and about 18° C.

26. The method of claim 24, wherein positioning the applicator comprises adhesively securing the applicator.

27. The method of claim 24, wherein positioning the applicator comprises securing the applicator over the subject's forehead region.

28. The method of claim 24, wherein the method of enhancing sleep in a subject is a method of sustaining sleep in a subject with insomnia.

29. The method of claim 24, further comprising warming the thermal transfer region to a neutral temperature.

30. The method of claim 24, further comprising maintaining, after the subject has fallen asleep, the thermal transfer region at a second temperature between about 10° C. and 25° C. for a second time period.

31. The method of claim 30, further wherein the second temperature is maintained by adjusting the temperature of the thermal transfer region based on feedback from the patient.

32. The method of claim 30, further comprising ramping the temperature of the thermal transfer region from ambient temperature to the between about 10° C. and about 25° C. over at least five minutes.

33. The method of claim 30, further wherein the second temperature is maintained by adjusting the temperature of the thermal transfer region based on feedback from the patient.

34. A method of enhancing sleep in a subject by non-invasively applying hypothermal therapy to the subject's frontal cortex, prefrontal cortex, or frontal and prefrontal cortex, the method comprising:

positioning an applicator comprising a thermal transfer region in communication with the subject's skin over at least a portion of the subject's frontal cortex, prefrontal cortex, or frontal and prefrontal cortex;

cooling the thermal transfer region to between about 10° C. and about 25° C.; and maintaining, after the subject has fallen asleep, the thermal transfer region between about 10° C. and 25° C. while maintaining contact between the subject's skin over at least a portion of the subject's frontal cortex, prefrontal cortex or frontal and prefrontal cortex extending at least 30 minutes.

* * * * *

UNITED STATES PATENT AND TRADEMARK OFFICE
CERTIFICATE OF CORRECTION

PATENT NO. : 9,669,185 B2
APPLICATION NO. : 14/749590
DATED : June 6, 2017
INVENTOR(S) : Eric A. Nofzinger Page 1 of 1

It is certified that error appears in the above-identified patent and that said Letters Patent is hereby corrected as shown below:

On the Title Page

Item (73); after "Assignee: University of Pittsburgh – Of the Commonwealth System of Higher Education," delete "San Carlos, CA (US)" and insert --Pittsburgh, PA (US)--.

Signed and Sealed this
Thirty-first Day of March, 2020

Andrei Iancu
*Director of the United States Patent and Trademark Office*